(12) United States Patent
Crosetto

(10) Patent No.: US 7,132,664 B1
(45) Date of Patent: Nov. 7, 2006

(54) METHOD AND APPARATUS FOR IMPROVING PET DETECTORS

(76) Inventor: Dario B. Crosetto, 900 Hideway Pl., DeSoto, TX (US) 75115

( * ) Notice: Subject to any disclaimer, the term of this patent is extended or adjusted under 35 U.S.C. 154(b) by 270 days.

(21) Appl. No.: 10/706,821

(22) Filed: Nov. 10, 2003

Related U.S. Application Data

(60) Provisional application No. 60/424,933, filed on Nov. 9, 2002.

(51) Int. Cl.
   *G01T 1/202* (2006.01)

(52) U.S. Cl. .................................... 250/367; 250/36

(58) Field of Classification Search ............. 250/367, 250/368, 369, 363.03, 370.11
   See application file for complete search history.

(56) References Cited

U.S. PATENT DOCUMENTS

| | | | |
|---|---|---|---|
| 4,559,597 A | 12/1985 | Mullani | |
| 4,563,582 A | 1/1986 | Mullani | |
| 4,642,464 A | 2/1987 | Mullani | |
| 4,677,299 A | 6/1987 | Wong | |
| 4,743,764 A * | 5/1988 | Casey et al. ........... | 250/363.03 |
| 4,755,679 A | 7/1988 | Wong | |
| 4,823,016 A * | 4/1989 | Yamashita et al. ..... | 250/363.03 |
| 4,864,138 A | 9/1989 | Mullani | |
| 4,883,966 A | 11/1989 | Wong | |
| 4,929,835 A * | 5/1990 | Yamashita et al. .......... | 250/367 |
| 5,210,420 A | 5/1993 | Hartz et al. | |
| 5,227,633 A * | 7/1993 | Ryuo et al. ............... | 250/367 |
| 5,241,181 A | 8/1993 | Mertens et al. | |
| 5,272,344 A | 12/1993 | Williams | |
| 5,300,782 A | 4/1994 | Johnson et al. | |
| 5,319,204 A * | 6/1994 | Wong .................... | 250/363.03 |
| 5,329,124 A * | 7/1994 | Yamamoto et al. ......... | 250/367 |
| 5,430,229 A | 7/1995 | Voss | |

(Continued)

FOREIGN PATENT DOCUMENTS

CA 1245375 11/1988

(Continued)

OTHER PUBLICATIONS

U.S. Appl. No. 60/204,900, filed May 16, 2000, Crosetto.

(Continued)

*Primary Examiner*—Albert Gagliardi
(74) *Attorney, Agent, or Firm*—Jones Day; Brett Lovejoy

(57) ABSTRACT

The present invention is directed to a system, method and software program product for implementing 3-D Complete-Body-Screening medical imaging which combines the benefits of the functional imaging capability of PET with those of the anatomical imaging capability of CT. The present invention enables execution of more complex algorithms measuring more accurately the information obtained from the collision of a photon with a detector. The present invention overcomes input and coincidence bottlenecks inherent in the prior art by implementing a massively parallel, layered architecture with separate processor stacks for handling each channel. The prior art coincidence bottleneck is overcome by limiting coincidence comparisons to those with a time stamp occurring within a predefined time window. The increased efficiency provides the bandwidth necessary for increasing the throughput even more by extending the FOV to over one meter in length and the execution of even more complex algorithms.

19 Claims, 13 Drawing Sheets

U.S. PATENT DOCUMENTS

| | | | |
|---|---|---|---|
| 5,453,623 | A | 9/1995 | Wong et al. |
| 5,602,395 | A | 2/1997 | Nellemann et al. |
| 5,608,221 | A | 3/1997 | Bertelson et al. |
| 5,703,369 | A | 12/1997 | Mori |
| 5,753,917 | A | 5/1998 | Engdahl |
| 5,757,006 | A | 5/1998 | DeVito et al. |
| 5,760,401 | A | 6/1998 | Nelleman et al. |
| 5,841,140 | A | 11/1998 | McCroskey et al. |
| 5,847,396 | A | 12/1998 | Lingren et al. |
| 5,907,593 | A | 5/1999 | Hsieh et al. |
| 5,937,202 | A | 8/1999 | Crosetto |
| 5,949,842 | A | 9/1999 | Schafer et al. |
| 5,969,358 | A | 10/1999 | DiFilippo et al. |
| 5,986,266 | A | 11/1999 | Andreaco et al. |
| 5,998,793 | A | 12/1999 | Shao et al. |
| 6,008,493 | A | 12/1999 | Shao et al. |
| 6,035,013 | A | 3/2000 | Orava et al. |
| 6,140,650 | A | 10/2000 | Berlad |
| 6,297,506 | B1 * | 10/2001 | Young et al. ............... 250/369 |

FOREIGN PATENT DOCUMENTS

| | | |
|---|---|---|
| CA | 2252993 | 5/2000 |

OTHER PUBLICATIONS

U.S. Appl. No. 60/215,667, filed Jun. 30, 2000, Crosetto.
U.S. Appl. No. 60/250,615, filed Nov. 30, 2000, Crosetto.
U.S. Appl. No. 60/258,204, filed Dec. 20, 2000, Crosetto.
U.S. Appl. No. 60/261,387, filed Jan. 15, 2001, Crosetto.
U.S. Appl. No. 60/309,018, filed Jul. 31, 2001, Crosetto.
U.S. Appl. No. 60/424,933, filed Nov. 9, 2002, Crosetto.
Karp, Joel S. et al., "Performance Standards in Positron Emission Tomography," Journal of Nuclear Medicine, Dec. 1991, pp. 2342-2350, vol. 12, No. 32.
Watson, C.C. et al., "Design and Performance of a Single Photo Transmission Measurement for the ECAT ART," Siemens ECAT ART.
Seidel, J. et al., "Experimental Estimates of the Absolute Sensitivity of a Small Animal PET Scanner with Depth-of-Interaction Capability,", EEEE 2000-777.
Technical Data, "Nuclear Medicine/PET, Discovery VI," GE Medical Systems, Feb. 2002.
"Advance NXi, Whole-Body Positron Emission Tomography System S9110NF/S9110NM," GE Medical Systems, 2000.
Johnston, Brian D. et al., "Automated Data Acquisition and Analysis for Evaluation of PET Detector Units," General Electric Systems, pp. 873-875, Milwaukee, WI.
Lewellen, T.K. et al., "Investigation of the Performance of the General Electric Advance Positron Emission Tomograph in 3D Mode," IEEE Transactions on Nuclear Medicine, Aug. 1996, pp. 2199-2206, vol. 43, No. 4.
Lewellen, T.K. et al., "Investigation of the Count Rate Performance of General Electric Advance Positron Emission Tomograph," IEEE Transactions on Nuclear Science, Aug. 1995, pp. 1051-1057.
Smith, R.J. et al., "A Practical Method for Randoms Subtraction in Volume Imaging PET from Detector Singles Countrate Measurements," University of PA, Dept. of Radiology, 1996, pp. 992-996, Philadelphia, PA.
Cutler, P. Duffy et al., "An Approximate Method for Acquisition and Reconstruction of Volumetric PET Data," IEEE, 1994, pp. 1209-1211.
Smith, Robin J. et al., "The Countrate Performance of the Volume Imaging PENN-PET Scanner," IEEE Transactions on Medical Imaging, Dec. 1994, pp. 610-618, vol. 13, No. 4.
Moisan, c. et al., "A Count Rate Model for PET and Its Applications to an LSO HR PLUS Scanner," IEEE< 1997, pp. 1186-1190.
Budinger, Thomas F., "PET Instrumentation: What are the Limits?" Seminars in Nuclear Medicine, Jul. 1998, pp. 247-267, vol. XXVIII, No. 3.
Wear, James A., "A Model of the High Count Rate Performance of NaI (Tl)-Based PET Detectors," IEEE, 1998, pp. 1203-1207.
Smith, R.J. et al., "Methods to Optimize Whole Body Surveys with C-PET Camera," IEEE, 2000.
Kops, Elena Rota et al., "Performance Characteristics of an Eight-Ring Whole Body PET Scanner," Journal of Computer Assisted Tomography, 1990, pp. 437-445, vol. 14, No. 3.
Cherry, Simon R., "Recent advances in instrumentation for positron emission tomography," Nuclear Instruments & Methods in Physics Research, 1994, pp. 577-582.
Paans, A.M.J., "The Imaging of Positron Emitters in Single Photon and Coincidence Mode: Evaluation of SPECT and PET Systems," 18th Annual International Conference of the IEEE Engineering in Medicine and Biology Society, Amsterdam, 1996, 3.6.2.: PET and SPECT Imaging.
Karp, J.S., et al., "Performance Measurements for the GSO-based Brain PET Camera (G-PET)," University of PA, Dept. of Radiology.
Bandettini, A. et al., "An electronic coincidence triggering system for 'in-frame' DAQ from a double side µ-strip silicon detector exposed to X-rays," IEEE, 1993, pp. 517-519.
Mankoff, D.A. et al., "A local coincidence triggering system for PET tomographs composed of large-area positron-sensitive detectors," IEEE Transactions on Nuclear Science, Apr. 1990, pp. 730-736, vol. 37, No. 2.
Dent, H.M. et al., "A real time digital coincidence processor for positron emission tomography," IEEE Transactions on Nuclear Science, Feb. 1986, pp. 556-559-vol. 33, No. 1.
Mertens, J.D. et al., "Digital Coincidence Detection: A Scanning VLSI Implementation," IEEE Transactions on Nuclear Science, Dec. 1993, vol. 40.
Karp, J.S. et al., "Event localization in a continuous scintillation detector using digital processing," IEEE Transactions on Nuclear Science, Feb. 1986, pp. 550-555, vol. 33, No. 1.
Freifelder, Richard, "Design and Performance of the Head PENN-PET Scanner," IEEE Transactions on Nuclear Science, Aug. 1994, pp. 1436-1440, vol. 41, No. 4.
Karp, J.S. et al., "Factors Affecting Accuracy and Precision in PET Volume Imaging," Journal of Cerebral Blood Flow and Metabolism, 1991, pp. A38-A-44, vol. 11.
Karp, Joel S., "Effect of Increased Axial Field of View on the Performance of a Volume PET Scanner," Nuclear Science Symposium and Med. Imaging Conference, 1991, Conference Record of the 1991 IEEE, 1991, pp. 1574-1578, vol. 3.
Karp, J.S. et al., "Evaluation of Volume Imaging with the Head PENN-PET Scanner," University of PA, Department of Radiology, 1995, IEEE, 1995, pp. 1877-1881.
Karp, Joel S. et al., "Three-Dimensional Imaging Characteristics of the Head PENN-PET Scanner," Journal of Nuclear Medicine, Apr. 1997, pp. 636-643, vol. 38, No. 4.
Technical Data, ECAT® ACCEL Tomograph.
Saoudi, A. et al., "Investigation of Depth-of-Interaction by Pulse Shape Discrimination in Multicrystal Detectors Read Out by Avalanche Photodiodes," NSS Conference, 1998 IEEE, 1998, pp. 1078-1082, vol. 2.
Freifelder, R. et al., "Data acquisition with a positron emission tomograph," http://www.lecroy.com/lrs/EPP/freif.htm.
Newport, D.F. et al., "An ASIC Implementation of Digital Front-End Electronics for a High Resolution PET Scanner," IEEE Transactions on Nuclear Science, Aug. 1993, pp. 1017-1019, vol. 40, No. 4.
Paulus, Michael J. et al., A Low-Noise, Wide-Band CMOS Charge-sensitive Preamplifier for use with APD/LSO PET Detectors, IEEE Transactions on Nuclear Science, Jun. 1996, pp. 1666-1671, vol. 43, No. 3.
Shao, Yiping, "A Study of Depth of Interaction Measurement Using Bent Optical Fibers," Crump Institute of Biological Imaging, Dept. of Molecular and Medical Pharmacology, UCLA School of Medicine, 1999, pp. 1440-1444.
Derenzo, S.E., "Initial Characterization of a Positron-Sensitive Photodiode/BGO Detector for PET," IEEE Transactions for Nuclear Science, Feb. 1989, pp. 1084-1089, vol. 36, No. 1.
Huber, J.S., "Calibration of a PET Detector Module that Measures Dept of Interaction," IEEE Transactions on Nuclear Science, Jun. 1998, pp. 1268-1272, vol. 45, No. 3.

Yamamoto, S., "A GSO depth of interaction detector for PET," IEEE Transactions on Nuclear Science, Jun. 1998, pp. 1078-1082, vol. 45, No. 3.

Young, J.W. et al., "Optimum Bandwidth Usage in Digital Coincidence Detection for PET," CTI PET Systems, Inc., 1994, pp. 1205-1208.

Muehllehner, G. et al., "A hexagonal bar positron camera: problems and solutions," IEEE Transactions on Nuclear Science, Feb. 1983, pp. 652-659, vol. NS-30, No. 1.

Jones, W.F. et al., "Next Generation PET Data Acquisition Architectures," NSS 95 Conference Record, 1997, pp. 1202-1207, vol. 44, No. 3.

Binkley, David M. et al., "A Custom CMOS Integrated Circuit for PET Tomograph Front-End Applications," IEEE, 1994, pp. 867-871.

Cutler, P. Duffy et al., "Use of Digital Front-End Electronics for Optimization of a Modular PET Detector," IEEE Transactions on Medical Imaging, Jun. 1994, pp. 408-418, vol. 13, No. 2.

Young, John W. et al., "FPGA Based Front-End Electronics for a High Resolution PET Scanner," CTI PET Systems, Inc.

Yu, Haiming et al., A High-Speed and High-Precision Winner-Select-Output (WSO) ASIC, pp. 656-660, University of Washington Medical Center, Seattle, WA.

Stenstrom, P. et al., "Evaluation of a Data Acquisition System for SPECT (PET)," IEEE, 2000.

Z.He et al., Two Data Acquisition And Processing Systems For A Compact Gamma-Camera, IEEE Transactions on Nuclear Science, Aug. 1993, pp. 1165-1168, vol. 40, No. 4.

Cherry, Simon R. et al., "Optical Fiber Readout of Scintillator Arrays using a Multi-Channel PMT: A High Resolution PET Detector for Animal Imaging," IEEE Transactions on Nuclear Science, Jun. 1996, pp. 1932-1937, vol. 43, No. 3.

Lewellen, T.K. et al., "An XYE Acquisition Interface for General Electric Starcam Anger Cameras," University of Washington, Seattle, Washington, pp. 1861-1865.

Lewellen, T.K. et al., "A Data Acquisition System for Coincidence Imaging Using a Conventional Dual Head Gamma Camera," IEEE, 1997, pp. 1305-1309.

Binkley, David M. et al., "An Electronic Detector Simulator for Testing Positron, Energy, and Timing Spectral Performance of Detector Electronics," CTI PET Systems, Inc., No Date.

Li, Hong Di et al., "Electronics for a Prototype Variable Field of View PET Camera Using the PMT-Quadrant-Sharing Detector Array," IEEE, 1999, pp. 1227-1231.

Binkley, David M. et al., "A Monolithic 2μm CMOS Constant-Fraction Discriminator for Moderate Time Resolution Systems," IEEE Transactions on Nuclear Science, Dec. 1991, pp. 1754-1759, vol. 38, No. 6.

Huber, J.S. et al., "Characterization of a 64 Channel PET Detector Using Photodiodes for Crystal Identification," IEEE Transactions on Nuclear Science, Jun. 1997, pp. 1197-1201, vol. 44, No. 3.

Siegel, Stefan et al., "Development of Continuous Detectors for a High Resolution Animal PET System," IEEE Conference Record, 1994, pp. 1662-1666.

Huber, J.S. et al., "Conceptual Design of a High-Sensitivity Small Animal PET Camera with 4π Coverage," IEEE Transactions on Nuclear Science, Jun. 1999,m pp. 498-502, vol. 46, No. 3.

Moses, W.W., et al. "Performance of a PET Detector Module Utilizing an Array of Silicon Photodiodes to Identify the Crystal of Interaction," IEEE Transactions on Nuclear Science, Aug. 1993, pp. 1036-1040, vol. 40, No. 4.

Gruber, G.J. et al., "A Discrete Scintillation Camera Module Using Silicon Photodiode Readout of CsI(TI) Crystals for Breast Cancer Imaging," IEEE Transactions on Nuclear Science, Jun. 1998, pp. 1063-1068, vol. 45, No. 3.

Huber, J.S., "A LSO Scintillator Array for a PET Detector Module with depth of Interaction Measurement," IEEE, pp. 14-46-14-50.

Correia, J.A. et al., "Performance of Small Animal PET Instrument with 1mm Resolution," IEEE, 2000.

McIntyre, "A Positron Emission Tomograph Designed for 3/4 mm Resolution," IEEE, 1995, pp. 1357-1361.

Dahlbom, Magnus et al., "Design Study of Future 3-D PET Systems," IEEE, 1995, pp. 1667-1671.

Casey, M.E. et al., "Investigation of LSO Crystals for High Spatial Resolution Positron Emission Tomography," IEEE Transactions on Nuclear Science, Jun. 1997, pp. 1109-1113, vol. 44, No. 3.

Rogers, Joel G. et al., "Testing 144- and 256-crystal BGO Block Detectors," IEEE, NSS MIC Conference Record 1993, pp. 18370184l, vol. 3.

Moisan, C. et al., "Simulating the Performance of an LSO Based Position Encoding Detector for PET," IEEE, 1997, pp. 1211-1215.

Ficke, D.C. et al., "A GSO(Ce) Block Type Detector for High Count Rate PET Applications," IEEE, 1995, pp. 1859-1863.

Saoudi, A. et al., "A Novel APD-Based Detector Module for Multi-Modality PET/SPECT/CT Scanners," IEEE, 1999, pp. 1089-1093.

Lecomte, R. et al., "An APD-based Quad Scintillator Detector Module with Pulse Shape Discrimination Coding for PET," IEEE, 1999, pp. 1445-1447.

Lecomte, R. et al., "Investigation of GSO, LSO and YSO Scintillators using Reverse Avalanche Photodiodes," IEEE, 1998, 212-216.

Rogers, J.G. et al., "An Improved Multicrystal 2-D BGO Detector for PET," IEEE Transactions on Nuclear Science, 1992, pp. 1063-1068, vol. 39, No. 4.

Moses, William W. et al., "PET detector modules based on novel detector technologies," Nuclear Instruments and Methods in Physics Research A 353, 1994, pp. 189-194.

Del Guerra, A. et al., YAP-PET: a small animal Positron Emission Tomograph based on YAP:Ce finger crystals. No date.

Vittori, F. et al., "The YAP Camera: An accurate Gamma Camera Particularly Suitable for New Radiopharamceuticals Research," IEEE Transactions on Nuclear Science, Feb. 1997, pp. 47-53, vol. 44. No. 1.

Rogers, Joel G. et al., "A Practical Block Detector for a Depth Encoding PET CAmera," 1996, pp. 1637-1641.

Cherry, Simon R. et al., "A Comparison of PET Detector Modules Employing Rectangular and Round Photomultiplier Tubes," IEEE Transactions on Nuclear Science, Aug. 1995, pp. 1064-1068, vol. 42, No. 4.

Weinhard, Klaus et al., "Performance Evaluation of the Positron Scanner ECAT EXACT," Journal of Computer Assisted Tomography, Sep./Oct. 1992, pp. 804-813, vol. 16, No. 5.

Spinks, T.J. et al., "Performance of a new 3D-only PET scanner—the EXACT3D," IEEE 1997, pp. 1275-1279.

Spinks, T.J. et al., "Physical characteristics of the ECAT EXACT3D positron tomograph," Phys. Med. Biol., 2000, pp. 2601-2018.

Wienhard K. et a., "The ECAT HRRT: Performance and First Clinical Application of the New High Resolution Research Tomograph," No Date.

Dahlbom, M. et al., "Performance of a YSO/LSO Phoswich Detector for use in a PET/SPECT System," IEEE Transactions on Nuclear Science, Jun. 1997, pp. 1114-1120, vol. 44, No. 3.

Cherry, S.R. et al., "MicroPET: A High Resolution PET Scanner for Imaging Small Animals," IEEE Transactions on Nuclear Science, Jun. 1997, vol. 44, No. 3.

Dalbom, M. et al., "Whole-Body Positron Emission Tomography: Part 1. Methods and Performance Characteristics," Journal of Nuclear Medicine, Jun. 1992, pp. 1191-1199, vol. 33, No. 6.

Moreno-Cantu, J.J. et al., "Evaluation of the ECAT EXACT HR+ 3D PET Scanner in $^{15}$O-water Brain Activation Studies," IEEE, 1997, pp. 1280-1284.

Dahlbom, Magnus et al., "Methods for Improving Image Quality in Whole Body PET Scanning," IEEE Conference Record 1991, pp. 1587-1382.

Bruckbauer, T. et al., "Evaluation of the ECAT EXCAT HR with ACSII for Clinical Routine 3D Measurements," 1996, pp. 1378-1382.

Moreno-Cantu, J.J. et al., "Evaluation of the ECAT EXACT HR + 3D PET Scanner in $^{15}$O-water Brain Activation Studies: Dose Fractionation Strategies for rCBF and Signal Enhancing Protocols," IEEE Transactions on Medical Imaging, Dec. 1998, pp. 979-985, vol. 17, No. 6.

Shao, Yiping et al., "Evaluation of Multi-Channel PMT's for Readout of Scintillator Arrays," 1996, pp. 1055, 1059.

Schmand, M. et al., "Performance Evaluation of a New LSO High Resolution Research Tomography—HRRT," No Date.

Brix, Gunnar et al., "Performance Evaluation of a Whole-Body PET Scanner Using the NEMA Protocol," Journal of Nuclear Medicine, Oct. 1997, pp. 1614-1623.

Crosetto, Dario B., "A modular VME or IBM PC based data acquisition for multi-modality PET/CT scanners of difference sizes and detector types," Presented at the IEEE Nuclear Science Symposium and Medical Imaging Conference, Lyon, France, 2000, pp. 1-20.

Crosetto, Dario B., "Real-time, programmable, digital signal-processing electronics for extracting the information from a detector module for multi-modality PET/SPECT/CT scanners," Presented at the IEEE Nuclear Science Symposium and Medical Imaging Conference, Lyon, France, 2000, pp. 1-8.

Crosetto, Dario B., "Saving lives through early cancer detection: Breaking the current PET efficiency barrier with the 3D-CBS," Presented on May 16, 2001 at the University of Geneva, Switzerland.

Crosetto, Dario B., "400+ times improved PET efficiency for lower-dose radiation, lower-cost cancer screening," 2000, pp. 1-200.

Wienhard, Klaus et al., "The ECAT EXACT HR: Performance of a New High Resolution Positron Scanner," Journal of Computer Assisted Tomography, pp. 110-118; Jan./Feb. 1994.

DeGrado, Timothy R. et al., "Performance Characteristics of a Whole-Body PET Scanner," The Journal of Nuclear Medicine, Aug. 1994, pp. 1398-1406, vol. 35, No. 8.

Smith, Wesley et al., "Calorimeter Trigger," Technical Overview, DoE/NSF Review, pp. 1-29; http://www.hep.wisc,edu/wsmith/cms/Lehman98_Cal.pdf., May 1998.

Beigbeder, Christopher et al., "An Update of the 2×2 Implementation for the Level) Calorimeter Triggers," LHCb 99-007, pp. 1-15, Apr. 29, 1999.

Eisenhandler, Eric, "Hardware Triggers at the LHC," pp. 47-56.

Lackey, J. et al., "CMS Calorimeter Level 1 Regional Trigger—Conceptual Design," CMS Note 1998/074, Nov. 13, 1998.

Crosetto, Dario B., "Detailed Design of the Digital Electronics Interfacing Detectors, First-Level Triggers, and Higher Levels of Trigger with Flexible Configuration Parameters," LHCb 99-006, TRIG, Mar. 30, 1999.

Technical Data, "biograph—The Imager for Life," Siemens Medical Systems, Inc., Journal of Nuclear Medicine, May 2001, article 369, p. 998.

* cited by examiner

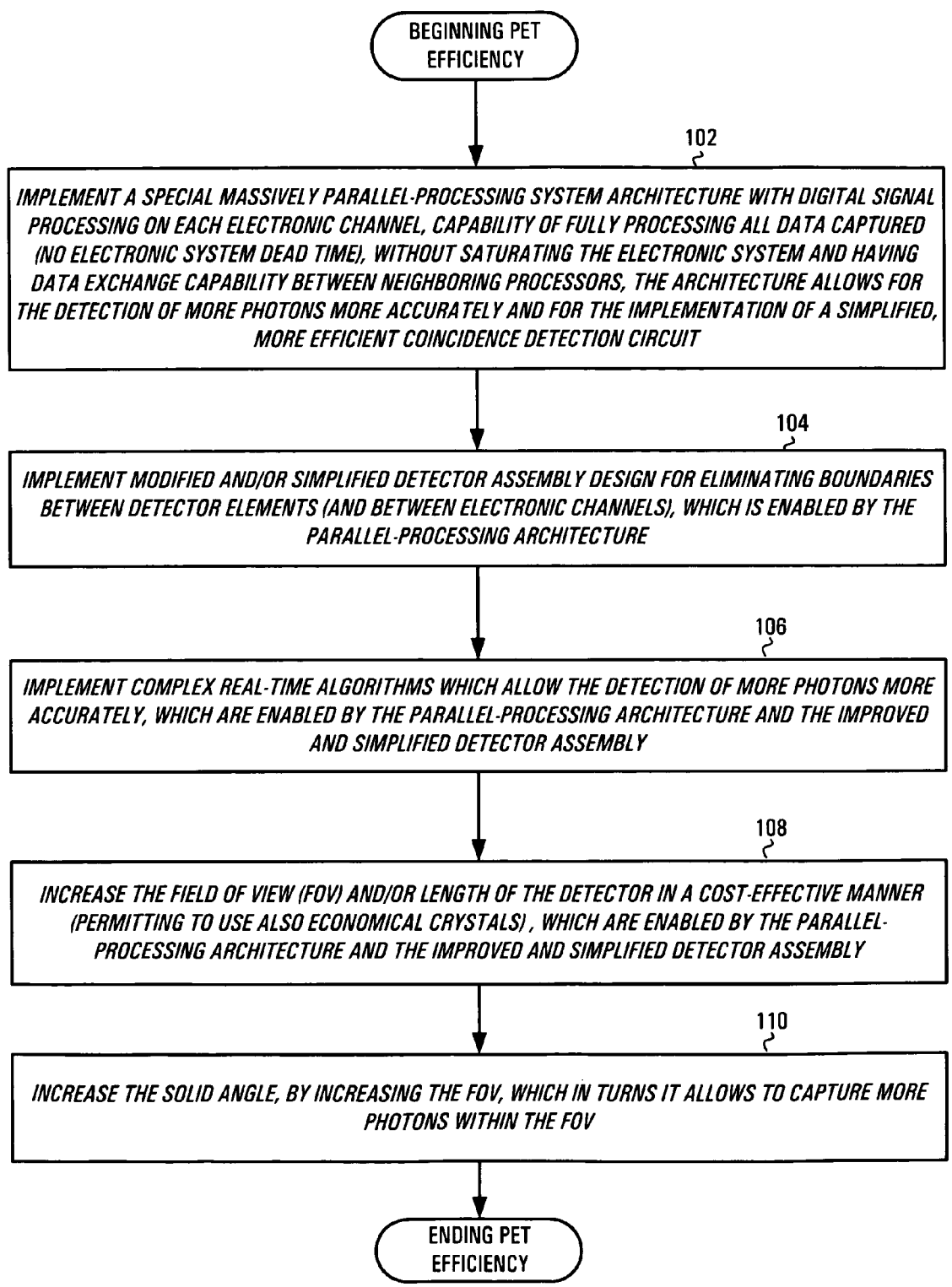

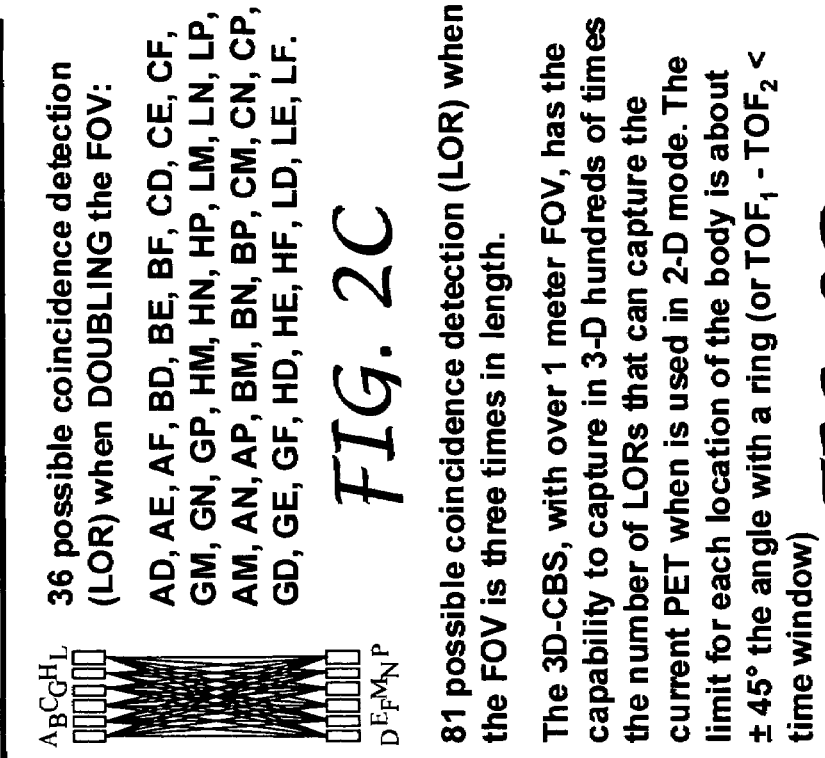
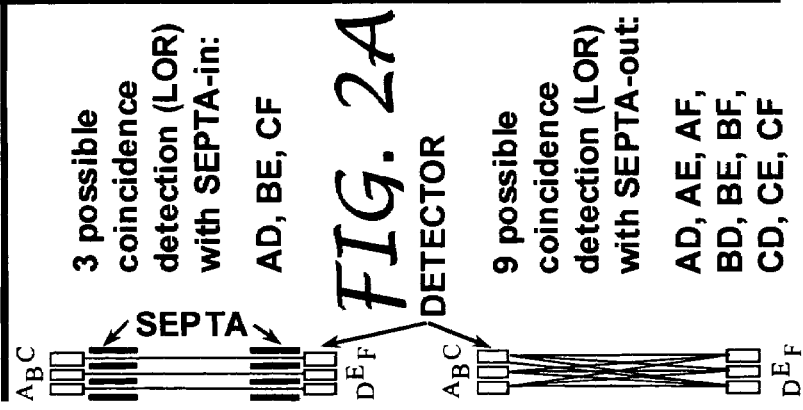

FIG. 2A — PRIOR ART PET with SHORT FOV: 3 possible coincidence detection (LOR) with SEPTA-in: AD, BE, CF

FIG. 2B — 9 possible coincidence detection (LOR) with SEPTA-out: AD, AE, AF, BD, BE, BF, CD, CE, CF

FIG. 2C — INCREASING THE FOV: 36 possible coincidence detection (LOR) when DOUBLING the FOV: AD, AE, AF, BD, BE, BF, CD, CE, CF, GM, GN, GP, HM, HN, HP, LM, LN, LP, AM, AN, AP, BM, BN, BP, CM, CN, CP, GD, GE, GF, HD, HE, HF, LD, LE, LF.

FIG. 2D — 81 possible coincidence detection (LOR) when the FOV is three times in length.

The 3D-CBS, with over 1 meter FOV, has the capability to capture in 3-D hundreds of times the number of LORs that can capture the current PET when is used in 2-D mode. The limit for each location of the body is about ±45° the angle with a ring (or $TOF_1 - TOF_2 <$ time window)

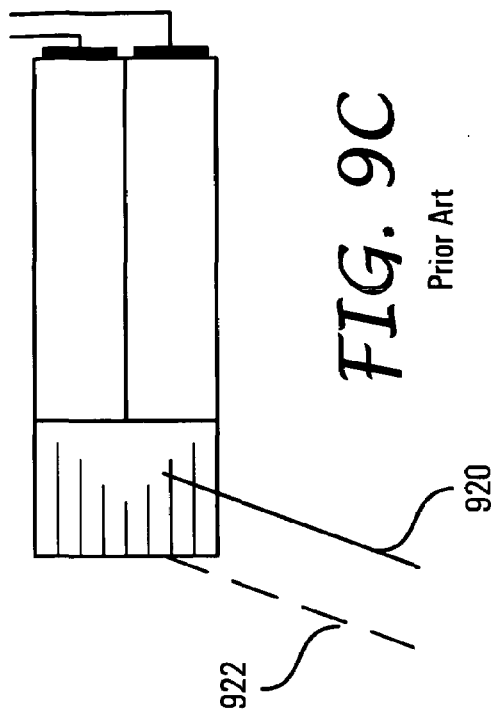
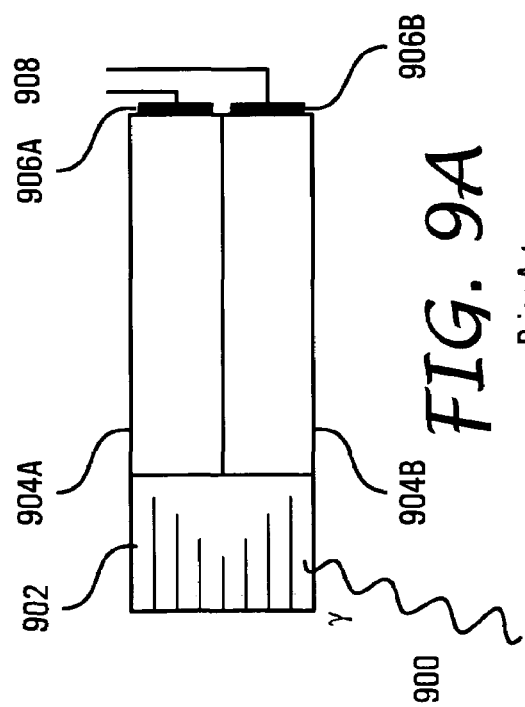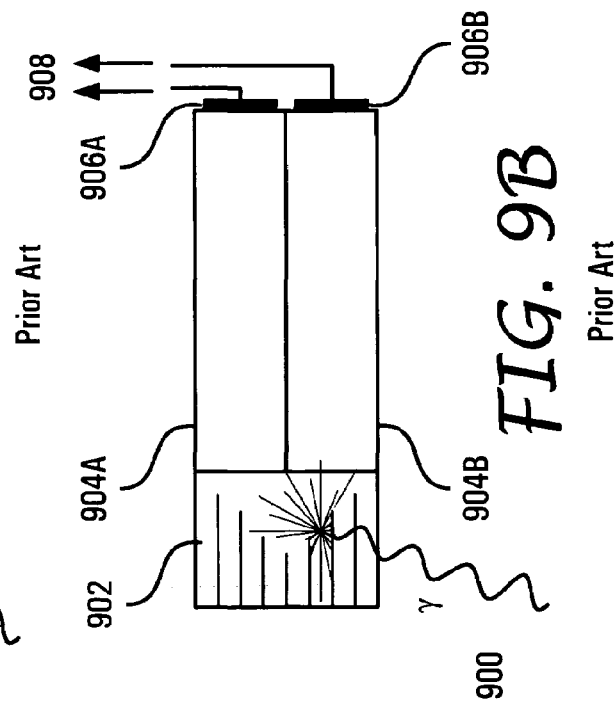

METHOD AND APPARATUS FOR IMPROVING PET DETECTORS

CROSS REFERENCES TO RELATED APPLICATIONS

The present application is related to and claims priority from the co-pending U.S. provisional patent application entitled "METHOD AND APPARATUS FOR IMPROVING PET DETECTORS" having application No. 60/424,933 filed on Nov. 9, 2002 and is incorporated by reference herein by reference in its entirety.

The present application is also related to the following patent applications:

U.S. Pat. No. 5,937,202 filed Feb. 15, 1996 entitled "High-Speed, Parallel, Processor Architecture for Front-End Electronics, Based on a Single Type of ASIC, and Method Use Thereof," (hereinafter U.S. patent '202).

U.S. patent application Ser. No. 09/506,207 filed Feb. 15, 2000 entitled "Method and Apparatus for Extending Processing Time in One Pipeline Stage," (hereinafter U.S. application '207), which claims priority from: U.S. Provisional Patent Application No. 60/120,194 filed Feb. 16, 1999; U.S. Provisional Patent Application No. 60/112,130 filed Mar. 12, 1999; U.S. Provisional Patent Application No. 60/129,393 filed Apr. 15, 1999; U.S. Provisional Patent Application No. 60/132,294 filed May 3, 1999; U.S. Provisional Patent Application No. 60/142,645 filed Jul. 6, 1999; U.S. Provisional Patent Application No. 60/143,805 filed Jul. 14, 1999; U.S. Provisional Patent Application No. 60/154,153, Sep. 15, 1999; U.S. Provisional Patent Application No. 60/161,458 filed Oct. 25, 1999; U.S. Provisional Patent Application No. 60/164,694 filed Nov. 10, 1999; and U.S. Provisional Patent Application No. 60/170,565 filed Dec. 14, 1999.

U.S. patent application Ser. No. 10/185,904 filed Jun. 27, 2002 entitled "Method and Apparatus for Whole-Body, Three-Dimensional Dynamic PET/CT Examination," (hereinafter U.S. application '904), claiming priority from U.S. Provisional Patent Application No. 60/301,545 filed Jun. 27, 2001; and U.S. Provisional Patent Application No. 60/309,018 filed Jul. 31, 2001.

U.S. patent application Ser. No. 10/296,532 filed Nov. 25, 2002 entitled "Method and Apparatus for Anatomical and Functional Medical Imaging," (hereinafter U.S. application '532), which claims priority from: PCT/US01/15671 filed May, 15, 2001; U.S. Provisional Patent Application No. 60/204,900 filed May 16, 2000; U.S. Provisional Patent Application No. 60/215,667 filed Jun. 30, 2000; U.S. Provisional Patent Application No. 239, 543 filed Oct. 10, 2000; U.S. Provisional Patent Application No. 60/250,615 filed Nov. 30, 2000; U.S. Provisional Patent Application No. 60/258,204 filed Dec. 22, 2000; and U.S. Provisional Patent Application No. 60/261,387 filed Jan. 15, 2001.

U.S. patent application Ser. No. 10/376,024 filed Feb. 26, 2003 entitled "Method And Apparatus For Determining Depth of Interactions in a Detector for Three-Dimensional Complete Body Screening," (hereinafter U.S. application '024), claiming priority from U.S. Provisional Patent Application No. 60/360,301 filed Feb. 26, 2002.

U.S. patent application Ser. No. 10/453,255 filed Jun. 2, 2003 entitled "Gantry for Geometrically Configurable and Non-Configurable Positron Emission Tomography Detector Arrays," (hereinafter U.S. application '255), claiming priority from U.S. Provisional Patent Application 60/385,140 filed Jun. 2, 2002.

The above-identified patent applications are incorporated by reference herein by reference in their entireties.

BACKGROUND OF THE INVENTION

1. Field of the Invention

The present invention relates to positron emission tomography (PET). More particularly, the present invention relates to PET detectors used therein.

2. Description of Related Art

The use of positron emissions for medical imaging has been well documented from the early 1950s, see "A History of Positron Imagining," Brownell, Gordon, presented on Oct. 15, 1999, Massachusetts General Hospital and available at http://neurosurgery.mgh.harvard.edu/docs/PEThistory.pdf, which is incorporated herein by reference in its entirety. PET imaging has advantages over other types of imaging procedures. Generally, PET scanning provides a procedure for imaging the chemical functionality of bodily organs rather than imaging only their physical structure, as is commonly available with other types of imaging procedures such as X-ray, Computerized Tomography (CT), or Magnetic resonance imaging (MRI). PET scanned images allow a physician to examine the functionality of the heart, brain, and other organs, as well as diagnosing disease groups which cause changes in the cells of a body organ or in the manner in which they grow, change, and/or multiply out of control, such as cancers.

Positron Emission Tomography (PET) is a medical imaging technique that involves injecting a natural compound, such as sugar or water, labeled with a radioactive isotope into a patient's body to reveal internal biological processes. As the isotope (positron) circulates within the patient's body. The positron annihilates with an electron and emits pairs of photons in diametrically opposed directions (back-to-back). A PET device is made of a set of detectors coupled to thousands of sensors that surround the human body. These detectors (crystals) capture the photons emitted by the isotope from within the patient's body at a total rate of up to hundreds of millions per second, while the sensors (transducers such as PMTs) convert them to electrical signals, and send the signals to the electronics.

Other applications for detecting particles (photons, electrons, hadron, muon and jets) are well known, such as with regard to experiments in high energy physics. While particle detection in high energy physics and medical imaging have some common ground, differences between the disciplines are sticking. One distinction between the usages is that the detectors used in medical imaging are approximately 200 times smaller than the larger detectors employed in high-energy physics applications, and what is more, medical imaging PET applications require the identification of only a single type of particle, the photon.

Typically, prior art Positron Emission Tomography (PET) devices require the injection into the patient's body of a radiation dose that is 10 to 20 times the maximum radiation dose recommended by the International Commission on Radiological Protection (ICRP). This amount is necessary because, at best, prior art PET devices detect only two photons out of 10,000 emitted in the patients' body. Currently, the largest manufacturers of PET (General Electric Company and Siemens AG (ADR)) which command in excess of 90% of the world market, are manufacturing two different PET (PET/CT) systems with very similar performance and are selling them at very similar prices. However, although the price and performance of the systems from the different manufacturers are comparable, one manufacturer's system (Siemens) uses nearly ideal crystal detectors, while contrastingly, the other manufacturer's system (General Electric) uses cheaper, lower quality crystal detectors with slower decay time. Consequently, the manufacturer using the cheaper, lower cost detectors, expends on the order of only 10% the price of the ideal crystals used in their competitor's systems. Thus, the question arises as to how it could be that, even though one manufacturer uses crystal detectors that are ten times more expensive that the other manufacturer, the price and performance of the two PET systems from the different manufacturers are very comparable.

Anecdotally, the present inventor has analyzed the progress of the most significant PET improvements made in the most recent 17 years, see "400+ times improved PET efficiency for lower-dose radiation, lower-cost cancer screening," 3D-Computing, Jun. 30, 20010, ISBN: 0970289707, which is incorporated herein by reference in its entirety. During that time period, the efficiency of PET improved at a rate of between two and three times every five years. The analysis included technical literature, patents (including those assigned to GE and Siemens) and also PETs that were built as prototypes at several universities but were never commercialized. At the current improvement rate of PET advancement, it would conservatively take several decades of improvements for the radiation dose necessary for a PET procedure to come within the maximum radiation dose recommended by the ICRP.

What is needed is a means for increasing the accuracy and efficiencies of PET devices enabling caregivers to more accurately diagnose aliments related to the functionality of body organs and not just inferences from the structure of the organs. Additionally, what is needed is a quantum advance forward in PET devices and procedures wherein patients can receive the benefits of PET imaging without the associative risks from the radioactive doses necessary for the procedures. Finally, what is needed is a means for reducing the associated risks and increasing detection efficiencies associated with PET imaging procedures to such an extent that the benefits of PET imaging can be applied in well-body care and preventative medicine strategies for apparently healthy individuals as a standard health assessment and diagnostic tool for regular, periodic checkups.

SUMMARY OF THE INVENTION

The present invention is directed to a system, method and software product for increasing the efficiency of a PET device. The present invention is directed to a series of improvements which are concatenated and relates to provide the efficiencies of over 400 times that of prior art PET devices.

A modular, digital system, fully programmable and scalable for a multi-modality, open (to accommodate claustrophobic or overweight patients, with the option of closing the detector, to increase efficiency), utilizing both Positron Emission Tomography (PET) and Computed Tomography (CT) in one unit is presented herein for VME and IBM-PC based platforms. The present invention fully exploits the double photon emission occurrence and allows for annual whole-body screening for cancer and other systemic anomalies; only 1/30 the radiation dosage; a reduction in scan time to 4 minutes for an axial Field of View (FOV) of 137.4 cm as opposed to 55 minutes for an axial FOV of 16 cm; a decrease in examination cost by 90%; an increase in sensitivity, providing physicians with additional clinical information on a specific organ or area and contribute to the specificity in detecting and assessing cancer.

The present system collects digital data from multiple electronic channels. Each electronic channel carries the information (64-bit) of all sensors included in a given view angle of the detector. The 64-bits data packets acquired at 20 MHz by each channel with zero dead-time are correlated with neighboring information and processed in real time by a DSP processor to improve the signal-to-noise ratio and extract and measure particle properties, resulting in the identification of the particle's position, accurate energy measurement, Depth of Current PET devices Interaction (DOI), and the timing measurements. A thorough real-time algorithm that best identifies the photons can be executed because the 3D-Flow sequentially-implemented, parallel architecture (SIPA) allows for processing time to be extended in a pipeline stage beyond the time interval between two consecutive input data by configuring by-pass switches in parallel with the processors. Very low power consumption drivers drive short, equal-length PCB traces between 3D-Flow chips, solving the problem of signal skew, ground bounce, cross-talk and noise. The electronics validate and separate events from the different modalities (PET/CT); PET events are checked for coincidences using a circuit sensitive to radiation activity rather than the number of detector elements. Both PET and CT examinations occur at the same time in a stationary bed position using a detector with a long axial FOV, avoiding motion artifacts, increasing throughput, reducing examination cost, reducing radiation to patients, increasing resolution, improving data quality, and reducing erroneous readings (false positives). The saturation of the electronics in prior art PET is overcome by using a system with an input bandwidth of 35 billion events per second distributed over 1,792 channels. The output bandwidth is selectable to sustain the activity generated by the maximum radiation that a PET/CT should ever receive.

The pipe-line architecture of the present invention runs contrary to that known in the prior art. Rather than a task being divided into incremental sub-tasks for execution of each processor in a pipeline circuit, the entire task is accomplished at a pipeline processor prior to the data moving out. When data enters a unit, it will stay there until the entire task is completed. The result will then "walk," one step at a time, through to the exit (stopping for one cycle at each register at each unit but without being further processed).

Also disclosed is a detector assembly capable of determining extremely accurate DOI measurements. A detector element assembly is coupled to a photomultiplier (PMT) at one end and to an Avalanche Photodiode (APD) at the other end. The APD size is typically smaller than the PMT (and crystal) size, thus a light guide conveys the light from the larger surface coupled to the crystal detector to the smaller area of the sensitive APD. The crystal is made of a single continuous block of material, or it can be made of two sections. One section is coupled to the PMT is a continuous (single) block of crystal. The entire detector (barrel or a section covering a large portion of the human body) can be made of a single piece of crystal which is then coupled to several PMTs. A second section is coupled to a previous crystal block in one side and is coupled to the light guide on the other side. This can be made of pixel (1×1 mm to 5×5 mm in size). A reflective material is placed between pixels in order to reduce on adjacent PMTs the spread of the light originated by the interaction of the incident photon with the crystal. The assembly of the detector provides the possibility to change the thickness of the entire crystal and the percentage of the thickness of the crystal with equal length reflecting slits compared to the solid crystal. The typical function of the PMT is to accurately measure the photon arrival time, its energy, and spatial resolution, while the function of the APD can be less important and just for a simpler function of providing the energy information on the other side of the crystal that would allow the calculation of the depth of Interaction (DOI). The purpose of the cut (slits) between small crystals (pixels) is to reduce the number of photomultipliers affected by the light generated by an event (or interaction between the incident photon and the crystal). The length of these cuts which separate two crystals has to be determined experimentally and is different from crystal to crystal. The optimal solution will be when the highest spatial resolution, low detector dead time, and good separation of pileup events is achieved. The optimal solution is determined by changing the centroid calculation and the pileup separation real-time algorithm, together with the change on the length of the slits. For some fast crystals, the cut of the crystals (slits) is not necessary.

Unlike prior art PET electronics which are typically implemented asynchronously, the electronics of the present invention is synchronous. The analog-to-digital converters can sample the signals from the PMT or APD synchronously or asynchronously. Typically, detectors with long decay time are sampled synchronously at a higher rate (two to five times faster than the decay time), while fast crystals can be sampled asynchronously with a fixed delay from when a trigger generated from the constant fraction discriminator occurs. In any event, regardless of the technique used, a constant fraction discriminator triggers on the photon's arrival time. This trigger signal is sent to a time-to-digital converter, which measures the photon's arrival time (with respect to the system clock).

The electronics in the 3D-Flow DSP photon detection board (the data reduction stack) can provide accurate information on all the above parameters (time-stamp, total energy, and DOI measurements) because each channel has a dedicated set of DSP processors. Those DSP can compute complex calculations on each signal that arrives from the PMT and can correlate that signal with the eight neighboring signals. Each has highly programmable computing capability and neighboring (eight, twenty-four, etc.) data exchange, allowing for the extraction of highly accurate spatial resolution information on the interaction between the photon and the crystal. The programmability of the present processors and its architecture allows the execution of any algorithm (i.e., any DOI measurement with any technique), even if it takes more time than the interval between any consecutive input data. The present invention can measure more accurately the total energy by summing the energy of the eight neighbors (rather than only three neighbors as implemented in the current PET). It also utilizes a narrower energy window for better separation of the scatter events from the good events and thereby achieves the goal of "rejecting more scattered events than good ones."

Higher efficiency and greater accuracy (image resolution) are made possible by summing eight neighbors or more with the head of a cluster, the calculation of the time-stamp, the execution with zero dead-time of a complex programmable real-time algorithm for a time longer than the time interval between two consecutive input data, and offers the possibility of extending the FOV in a cost-effective manner to capture a greater number of photons.

The calculation of the DOI on any of the three detector implementation techniques, and the centroid calculation based on the information from the eight neighbors on four sides preserves and increases the spatial resolution compared to the prior art "Anger Logic" technique which is based on information from just three neighbors from on only two sides.

The "time coincidence detection board," in addition to complementing the features of the "the photon detection board," increases the sensitivity of the PET by accepting through the LVDS serial input/output lines a string of 64-bit information relative to the photon found (or any bit string such as the standard PET link format). The information of the 64-bit string is specified in the proposal (page 18) and can be received from the proposed "3D-Flow DSP photon detection board" or from any other board providing information on the photon through LVDS links. The "time coincidence detection board" routes the data from several LVDS input lines to fewer output lines. Events with the same time-stamp are sorted and compared to different groups of detectors to find coincidences.

In accordance with an exemplary embodiment of the present invention, with another aspect of the present invention, the PET improves the energy resolution by calculating the total energy of the incident photon, even when the photon strikes a crystal coupled with the boundary of two PMT or APD, by using its capability to exchange data with eight (or twenty-four) neighbors with no effect of detector boundaries. Superior spatial resolution is achieved by calculating the "X" and "Y" position of the incident photon based on the information of all eight neighboring PMTs (or APDs) with respect to any PMT (or APD) element where the local maxima was found (instead of only three neighbors or limited by detector segmentation with boundaries as is implemented in the current PET). Additionally, a photon's arrival time is detected and used for assigning a time-stamp to each event. This arrival time is then examined for time coincidence with any acceptable opposite detector element that received a hit. Finally, the present invention provides the possibility of executing complex real-time algorithms (e.g., calculating DOI measurements based on different detector implementations) on high-rate incoming data by using the massively parallel 3D-Flow architecture.

BRIEF DESCRIPTION OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

FIG. 1 is a flowchart depicting the steps necessary for increasing the photon capture efficiency of a prior art PET to that disclosed in exemplary embodiments of the present invention;

FIGS. 2A–2D are diagrammatic comparisons of the relationship between the increasing FOV and Lines of Response (LORs) in accordance with exemplary embodiments of the present invention;

FIG. 7 graphically depicts a circuit which requires only six comparisons amongst four photons (A-B, A-C, A-D, B-C, B-D, and C-D) every sampling period of the signals from the detector in accordance with an exemplary embodiment of the present invention;

FIGS. 9A–9C depict a scintillation detector assembly as is well known in the prior art;

Figure 3A:
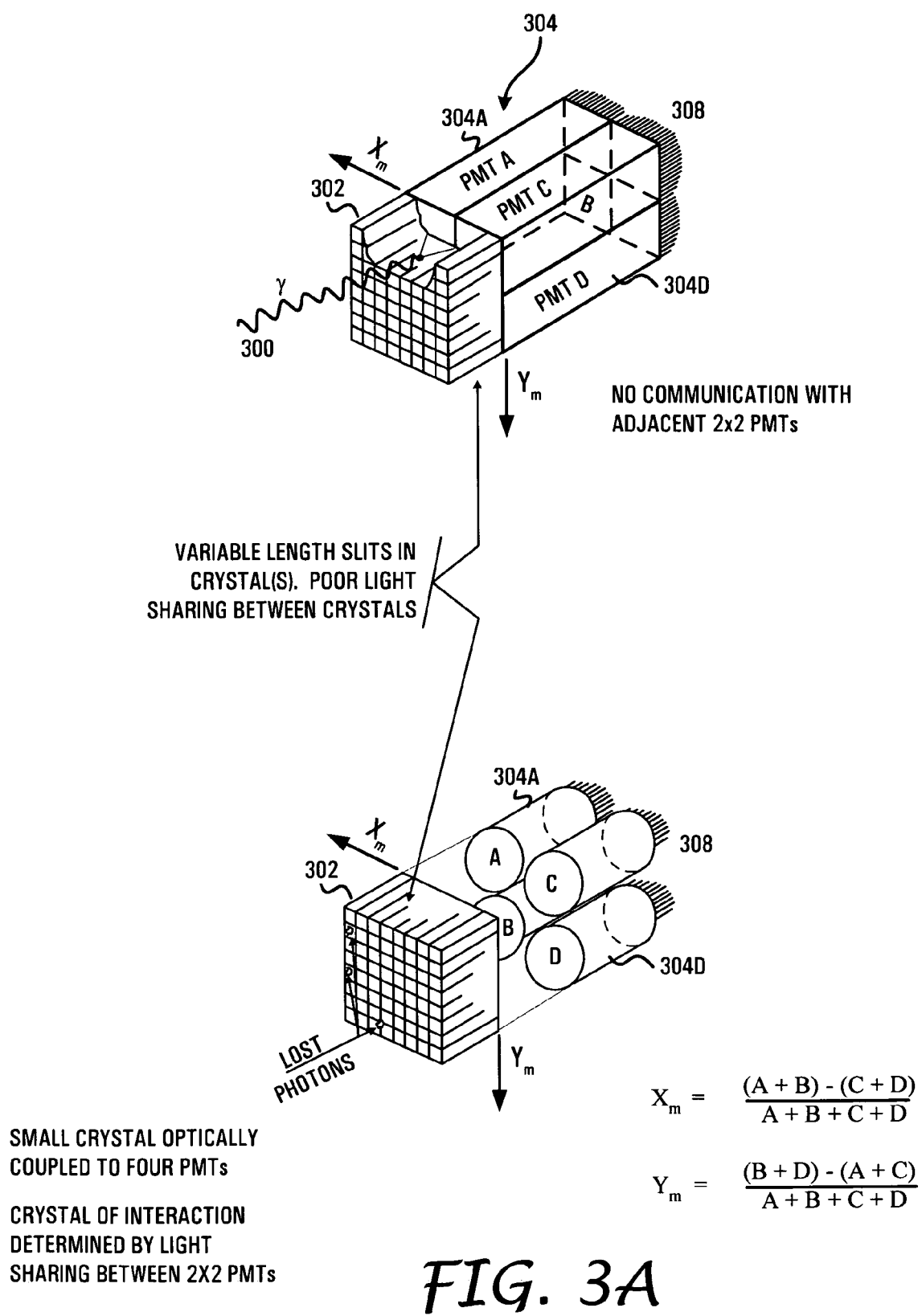
FIG. 3A is a diagram of a prior art detector crystal optically coupled to a 2×2 PMT module.

Other features of the present invention will be apparent from the accompanying drawings and from the following detailed description.

DETAILED DESCRIPTION OF THE INVENTION

The present invention, referred to internally herein as the three-dimensional complete body screening (3D-CBS) compared to the current Positron Emission Tomography (PET), encompasses a plurality of inventions disclosed herein and in related patents and co-pending patent applications identified throughout this disclosure. The scope of the corpus of inventions that comprises the 3D-CBS may not be fully appreciated without carefully examining the 3D-CBS from various perspectives which are important for medical professions that engage in human body scanning. Therefore, prior to discussing the exemplary embodiments of the present invention, the differences between the 3D-CBS system of inventions will be discussed with respect to a PET known in the prior art. Here, it should be understood that, although the 3D-CBS system will be discussed with regard to implementation in an exemplary embodiment of a PET, those of ordinary skill in the art will appreciate that the disclosed inventions are readily applicable to various types of tomography, such as Computerized Axial Tomography (CAT or CT), Single Photon Emission Computerized Tomography (SPECT) and PET CT. The following discussion examines the present 3D-CBS system with regard to increasing PET efficiency using the detection of coincident photon pairs as a metric, increasing image resolution and finally increasing patient usability.

FIG. 1 is a flowchart which illustrate an exemplary method for implementing the exemplary embodiments of the present invention on a prior art PET with regard to specific objectives. In particular, FIG. 1 is a flowchart depicting the steps necessary for increasing the photon capture efficiency of a prior art PET device to that disclosed in exemplary embodiments of the present invention. The PET efficiency described in the flowchart on FIG. 1 is further conditioned on all captured photons being identified as one pair of a coincident pair of photons (i.e., coincidence detection).

It is generally accepted by those practicing in the relevant art that primary source of poor PET efficiency resulting from lost photons results from inefficiencies in crystal detectors. While detector crystals do not have perfect stopping power and do not capture every photon in range, as measured by the industry and independent researchers, the operating efficiency of detector crystals has been demonstrated to be 80% to 95%. Thus, according to the industry, 80% to 95% of the photon incidences at a detector crystal are converted into electrical signals. By contrast, the inventor of the present invention has independently discovered that the efficiency of prior art PET electronic can be calculated at approximately 8% (discussed in greater detail below). Inefficient PET electronics is partially due to dead-time resulting from bottleneck (e.g., multiplexing of data from many lines to a single line, saturation on input, processing, saturation on output) present at any stage of the electronics. Another shortcoming of prior art PET electronics is saturation of the electronics at the output stage due to the limiting architecture of the coincidence detection circuitry. These and other shortcomings of the prior art have been overcome and the efficiency of PET devices improved by using a special massively parallel-processing system architecture with digital signal processing on each electronic channel in accordance with an exemplary embodiment of the present invention (step 102). The presently described processing system architecture is capable of fully processing all data captured (no electronic system dead time), without saturating the electronic system and further has data exchange capability between neighboring processors. The presently described processing system architecture allows for the detection of more photons, more accurately. Moreover, by implementing the presently described processing system architecture and overcoming the inherent inefficiencies of the prior art, the architecture allows for the detection of more photons and or the implementation of a simplified, more efficient coincidence detection circuit. The present architecture is described in greater detail below with respect to FIGS. 4–8.

Furthermore, the presently described processing system architecture allows for the implementation of a simplified detector assembly design for eliminating boundaries between detector elements (step 104). Additionally, boundaries between electronic channels are likewise eliminated because digital signal processors associated with each electronic channel have the capability to communicate with neighboring processors. Because the boundary is eliminated, a detector may share light with other detector crystals, which is converted into a signal by its transducer, and a processor can compare its channel signal with each of its neighbors for more reliable identification of photons. In any case, each electronic channel exchanges its data with all its neighbors over the entire detector. PET inefficiencies due to boundary limitations and their solutions are discussed below with regard to FIGS. 3A and 3B.

Additional improvements in PET efficiency are realized by executing complex real-time algorithms on the digital signal processors of each electronic channel in accordance with an exemplary embodiment of the present invention (step 106). The parallel-processing architecture and the improved and simplified detector assembly enable the execution of these algorithms, which, among other advantages, allow for the detection of more photons more accurately.

The parallel-processing architecture and the improved and simplified detector assembly increases the processing bandwidth making it possible to efficiently and accurately handle additional signals. Therefore, the PET device can be modified for captured additional photons, such as by increasing the Field of View (FOV) and/or length of the detector in a cost-effective manner (permitting to use also economical crystals) (step 108). Typically, the FOV of a prior art PET device is in the range of sixteen centimeters (16 cm). This equates to an efficiency for prior art PET devices in human scanning to approximately 0.02% at best because the radiation in the patient is in areas of the patient that are outside the FOV of a prior art PET device. The advantages of increasing the FOV are discussed below with regard to FIGS. 2A–2D. One result of the increasing the FOV is that the solid angle increases correspondingly, which in turns it allows the capture more photons within the FOV (step 110).

FIGS. 4A–4D are diagrams of a digital signal processing for implementation in current PET systems in accordance with an exemplary embodiment of the present invention. The design of circuit 400 is flexible enough to be used in several models of PET devices manufactured by various manufacturers.

In accordance with one exemplary embodiment of the present invention, the design specification of DAQ circuit 402 is as follows:

16 digital input channels (16-bit word-wide per channel);

Two input clocks at 20 MHz and 40 MHz with internal;

PLL on each FPGA chip that provides the internal timing at 320 MHz;

Two differential lines for output results (LVDS);

Time-to-digital converter measuring photon's arrival time on each channel with resolution of 500 ps;

Capability to execute in a programmable form, complex real-time algorithms with an execution time longer than the time interval between two consecutive input data. For instance, photon-detection algorithm, DOI measurements in PET or particle detection in HEP applications, or any real-time processing (graphic processing, data compression, etc.).

Capability of fast data exchange with neighboring 3D-Flow™ processors (North East, West, and South), which allows the correlation of signals that were split between several channels. This allows also clustering and local maxima calculation.

Capability to trigger on any channel that has been acquired and processed in parallel on all channels with zero dead time.

Capability to funnel results from 16 input channels to one (or two) output channels via routing algorithms executed on 20 processors 3D-Flow-pyramid accommodated in 5 FPGA chips.

Four serial I/O interfaces for 3D-Flow™ program loading, initialization, and system monitoring during data taking PCI interface;

The testability with: a) JTAG chain through the 29 large components; b) 70 LED; c) 120 test points at a 120-pin connector; and d) 50 test points scattered at different locations on the board which permit monitoring/debugging of critical functions/timing;

The board is designed to work: a) 'stand-alone' to process data at a high rate; b) in a system made of several boards controlled only by RS232; or c) stand-alone or in a system controlled by PCI interface;

The board is designed and implemented in such a way that any clock pin of any 3D-Flow™ FPGA chip in any board of the system (even when the boards belong to different crates or chassis) will not have a skew with any other 3D-Flow™ FPGA clock pin that will exceed 40 ps; and The high parallelism of the internal units of the 3D-Flow™ processor also allows the execution of complex real-time algorithms.

Each of processors 410 in one layer of the 3D-Flow stack 422 (see FIG. 4C) executes in parallel the real-time algorithm, from beginning to end, on data received from the PET detector, while processors at different layers of 3D-Flow stack 422 operate from beginning to end on different sets of data received from the PET detector. The present system architecture consists of several processors arranged in two orthogonal axes: one layer is an array of 3D-Flow processors 410, where each processor is interconnected to its four neighbors through North, East, West and South ports (see FIG. 4B). Several layers, assembled one adjacent to another to make a system, is called a "stack," represented in FIG. 4A as stack 422 which is responsible for photon detection and data reduction. The first layer is connected to the input sensors, while the last layer produces the results processed by all layers (layer A–D) in the stack, with the out-results sequenced in the precise order of the in-data from the input sensors (see FIG. 4D). Data and results flow through the stack from the sensors to the last layer. An electronic channel consists of one set of processors 410 connected from the bottom port of one chip to the top port of an adjacent chip (with the top port of the first chip connected to the signal received from the detector and the bottom port of the last chip connected to 3-D Flow pyramid 424). 3-D Flow pyramid 424 comprises coincidence circuitry through a pyramidal funneling structure of processor vertices.

The 3D-Flow architecture extends the execution time in a pipeline stage beyond the time interval between two consecutive input data using the bypass concept described in U.S. application '207, discussed immediately below.

Rather than requiring an ultra fast, expensive technology capable of executing several special instructions (e.g., data moving and data processing such as the 26 operations of the 3D-Flow) per second, or simplifying the real-time algorithm to the point that measurements such as energy, centroid, or DOI are not accurate, the 3D-Flow™ architecture permits the execution of complex algorithms and sustains a high input data rate using any technology (FPGA or ASIC at 0.25 micron or smaller for enhanced performance at a higher cost).

Figure 4A:
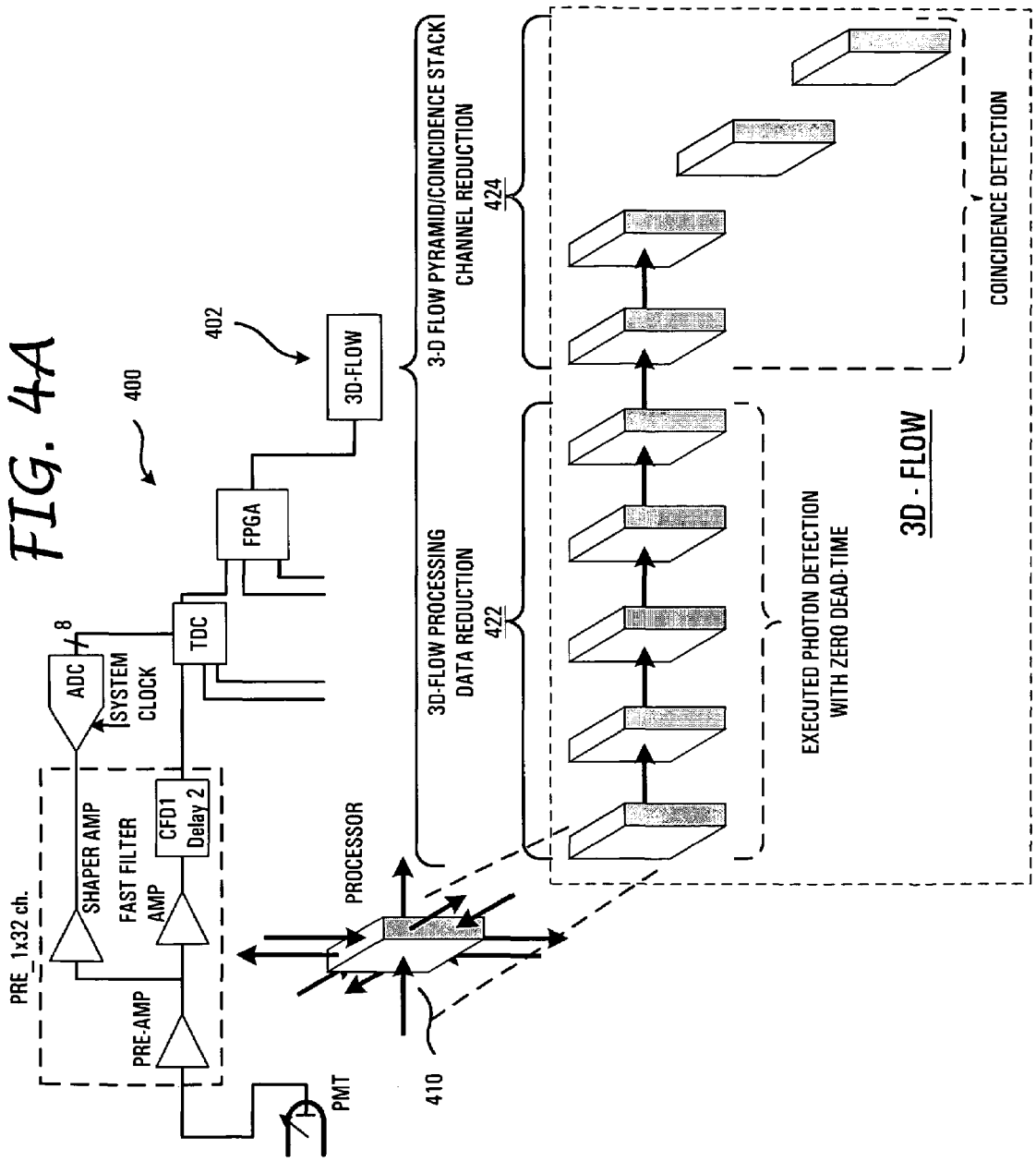
FIG. 4 is a diagram of a digital signal processor for implementation in current PET systems in accordance with an exemplary embodiment of the present invention.
Figure 4B:
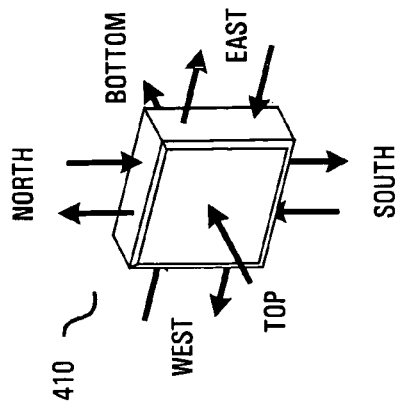
Figure 4D:
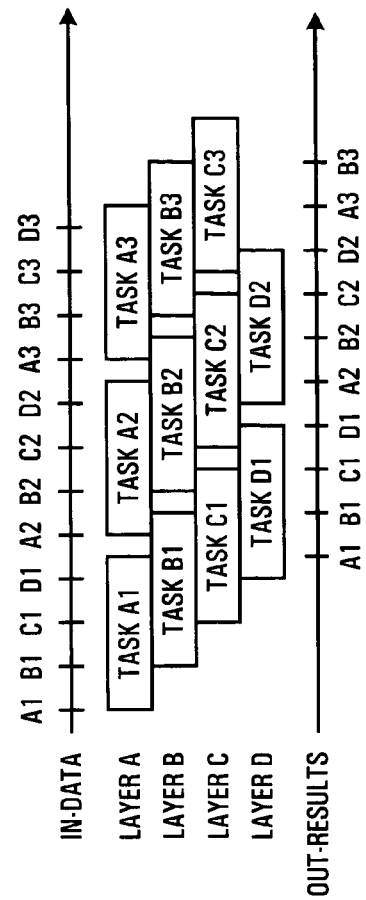
Figure 4C:
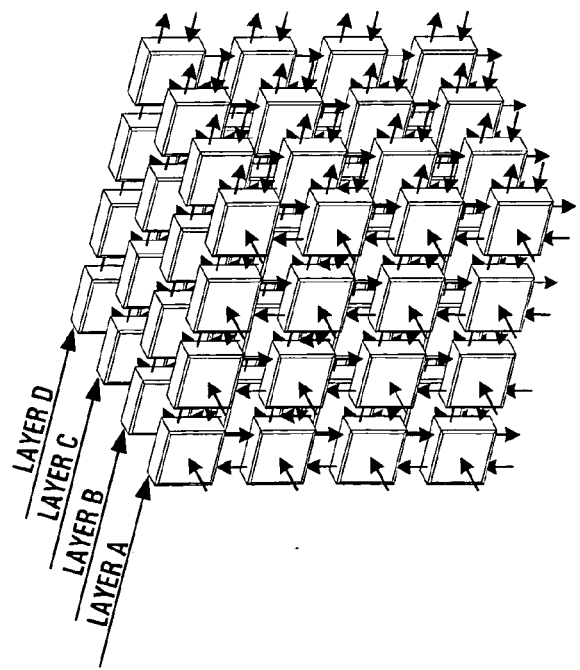

The extension by the 3D-Flow architecture of the execution time in a pipeline stage beyond the time interval between two consecutive input data is illustrated by the following example: an identical circuit (3D-Flow processor 410) is copied four times as shown in FIG. 4C. (The number of times the circuit is copied corresponds to the ratio between the algorithm execution time and the time interval between two consecutive input data.) A bypass switch coupled to each processor in each 3D-Flow in layer A sends one data packet to its processor and passes three input data packets and one output result from its processor along to the next layer. The bypass switches on the 3D-Flow processors at layer B send two input data packets along to the next layer, one output result received from layer A and one result from its processor, and so on. Only the processors at layer A are connected to the PET detector and these receive only input data. The processors at layer D send out only results. This architecture simplifies the connection in a parallel processing system and does not require a high fan-out from the detector electronics to send data to different processors of a parallel-processing system. All connections are point-to-point with several advantages in low power consumption, signal integrity, etc.

As discussed above, in order to understand what functions need improvement in order to increase PET efficiency, there must be an understanding of where photons are lost in a prior art PET device. Consequently, it should be appreciated that the lack of efficiency in prior art PET devices is not due to inefficiency in crystals, as has been believed in the past, but rather it was due to the inefficiency of the electronics, which also limits the detector assembly and the implementation of an efficient and accurate real-time photon-detection algorithm. The solution to overcome the inefficiency of current PET is a massively parallel-processing system at the front-end electronics of the PET device such as the one described immediately above, in which the present parallel-processing architecture can be implemented in FPGA or ASIC. Unlike other parallel-processing systems, the present invention allows for the execution of a programmable digital-processing algorithm on each electronic channel with neighboring-signal correlation. Additionally, the present circuitry can trigger on any electronic channel based on the shape of the pulse received or based on the information from a cluster of pulses from several neighboring elements centered on the highest pulse (or local maxima). Thus, it can accurately measure incident photon energy by summing 9, 16, or 25 elements, eliminating scattered events and separating events from the different modalities (PET/CT). It can accurately measure the spatial resolution by interpolating the value of the sum of three (or more) elements to the left of the local maxima and three (or more) elements to the right for both the X and Y positions. The high parallelism of the internal units of processor 410 allows for the execution of complex real-time algorithms to accurately measure DOI and eliminate parallax error of oblique photons. An oblique penetration of an incident photon into a crystal generates a parallax error if the depth of interaction (DOI) is not measured.

In accordance with an exemplary embodiment of the present invention, the first bottleneck described above is overcome by individually sampling each of the 1,344 channels at a rate of 20 MHz for a 64-bit word, sustainable continuously on all detectors using the massively parallel-processing system at the front-end electronics described above. A real-time algorithm that thoroughly checks all parameters characterizing a photon is executed on the data of an entire event and each channel is investigated to determine if it could be the head of a cluster (corresponding to the location of the incident photon). Furthermore, in accordance with another exemplary embodiment of the present invention, the processing time in one pipeline stage is extended using a series of bypass switches, which allows for the execution of real-time algorithms longer than the time interval between two consecutive input data (see specifically U.S. application '207). On the occasion where, for reasons other than the electronics (e.g., using as crystal slow decay time) where the rate of 20 MHz cannot be sustained for such, having the process flow handling each single channel of the 1,344 channels means that only one channel out of 1,344 (and not one out of 56 as is in the current PET) will be dead for the duration of the decay process in the crystal.

The second limitation of prior art electronics involves identifying photons in time coincidence. With regard to the prior art, a second bottleneck (in addition to the incoming data bottleneck) occurs in the coincidence electronics because prior art PET devices cannot handle a large number of acquisition channels, and therefore the number of channels is arbitrarily reduced to 56 channels. The reduction is based on a simple check to find out if a signal received from the sum of four channels is within a certain energy window.

The limitations in detecting coincidences of the prior art PET devices is brought about as a consequence of requiring the electronics to compare all pairs of signals from crystals which are points on a line passing through the patient's body. Using this approach, for a system with n channels, all possible comparisons (all Lines-Of-Response (LORs) of a PET) between all channels are: (n×(n-1)) divided by 2 (since only the crystals which are a point on a line passing through the patient's the result is further divided by 2. A prior art PET device with 56 modules must then perform about 700 comparisons along all LOR passing through the patient's body ((56×55)/2(2)=720. Moreover, by increasing the FOV from 15 cm to 140 cm, the number of 137 cm the number comparisons along all LOR passing through the patient's body is greatly increased.

In accordance with still another exemplary embodiment of the present invention, the ONLY photons that are compared are those whose characteristics show them to be a candidate for coincidence rather than comparing all LOR used in the current PET. To accomplish this, additional information relating to the photon is gathered upon detection (i.e., a time stamp), and affixed to the data signal upon exiting the data reduction stack (photon detection stack). Using the time-stamp for finding coincidences in a PET system is to identify all possible candidates within a predetermined sampling time, for example, 50 ns (no more than four candidates are expected for a radioactive dose of 5 mCi delivered to the patient and therefore only six comparisons are made for a coincidence only among those candidates). It is not necessary to test all LOR as is done by the prior art, but instead move fewer photon candidates for coincidence (less than four) to a coincidence circuit through a pyramidal funnelling structure.

An exemplary channel-reduction and time-coincidence board is disclosed herein for high-efficiency detection of photons in time coincidence in PET devices. The board comprises twenty processors (processor 410), each capable of executing up to 26 operations in a single cycle. These processors function identically when configured in the pyramidal funneling structure as when configured in the photon detection stack (2-D flow stack). Each processor can execute programmable real-time algorithms that route messages from the parallel Top processor input port or North, East, West, South LVDS serial input ports to the parallel Bottom processor output port or North, East, West, South LVDS serial output ports and can execute sorting and coincidence-detection algorithms. The board has a memory buffer (up to 512 MBytes) to store the attenuation correction coefficients and for de-randomizing and buffering data flow. It has 32 pairs of LVDS differential inputs and two pairs of LVDS differential outputs. Several transmission protocols can be implemented, including PETLINK protocol. Two in-phase clocks at 20 MHz and 40 MHz (with PLL×8=320 MHz internal clock) are distributed so as to limit the maximum skew between the clock of any processor in the system to less than 40 ps. The circuits are implemented in FPGA, and full programmability is dependent only on the real-time algorithms downloaded into the processor program memory. The board is suitable for the current PET with different detector types and for the 3D-CBS for best PET efficiency improvement. Typically, sixteen 3D-Flow DAQ boards are interfaced to one coincidence board.

The original sequences of the events as they were acquired by the detector, as well as their latency time from a location in a layer of the pyramid (funneling section of a 3D-Flow processing system) with respect to the time when they were created, are lost at the last stage of the pyramid (vertex). The reason is that events have followed different paths (short and long) when moved through the pyramid (see FIG. 5).

Figure 8:
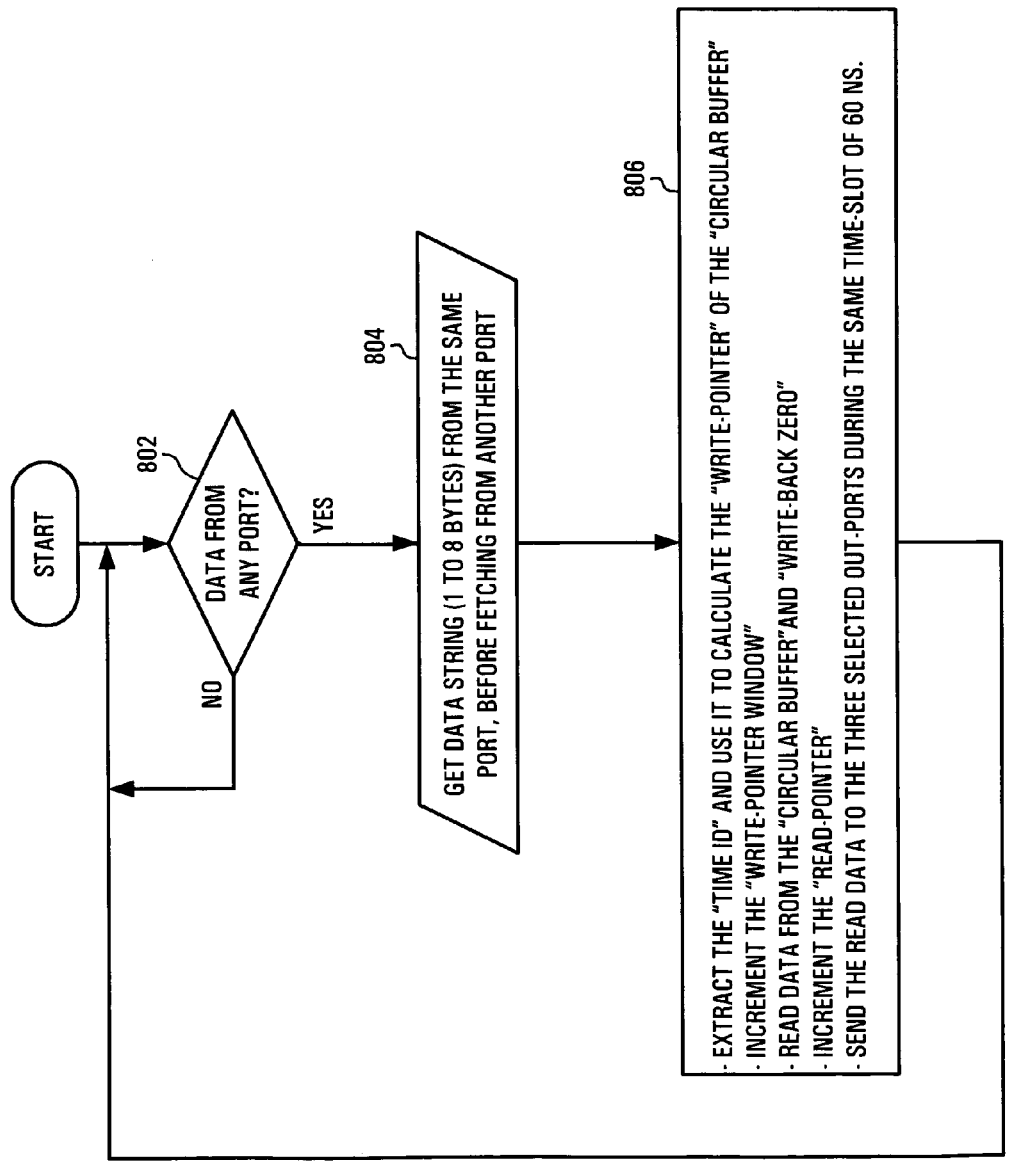
FIG. 8 is a flowchart depicting the sequence of operations for the implementation of the circular buffer for sorting and regaining fixed latency of events in accordance with an exemplary embodiment of the present invention.

The task of this stage (or vertex of the pyramid), which is implemented with a layer of 3D-Flow processors, is that of sorting the events in their original sequence (see sequence of operations in FIG. 8 and regaining the fixed latency time between data at different stages). FIG. 8 is a flowchart depicting the sequence of operations for the implementation of the circular buffer for sorting and regaining fixed latency of events in accordance with an exemplary embodiment of the present invention. The process begins with the determination that data are available at a port (step 802). The data string is read from the port prior to fetching data from another port (step 804). Finally, the "Time ID" is extracted from the data and the "write-pointer" of the "circular buffer" calculated from the "Time ID." The "write-pointer window" is incremented, data is read from the "circular buffer" and "write-back zero," the "read-pointer" is incremented and the read data is sent to the three selected out-ports during the same time-slot of 60 ns. sequence of operations implementing of the circular buffer for sorting and regaining fixed latency of events.

Figure 5:
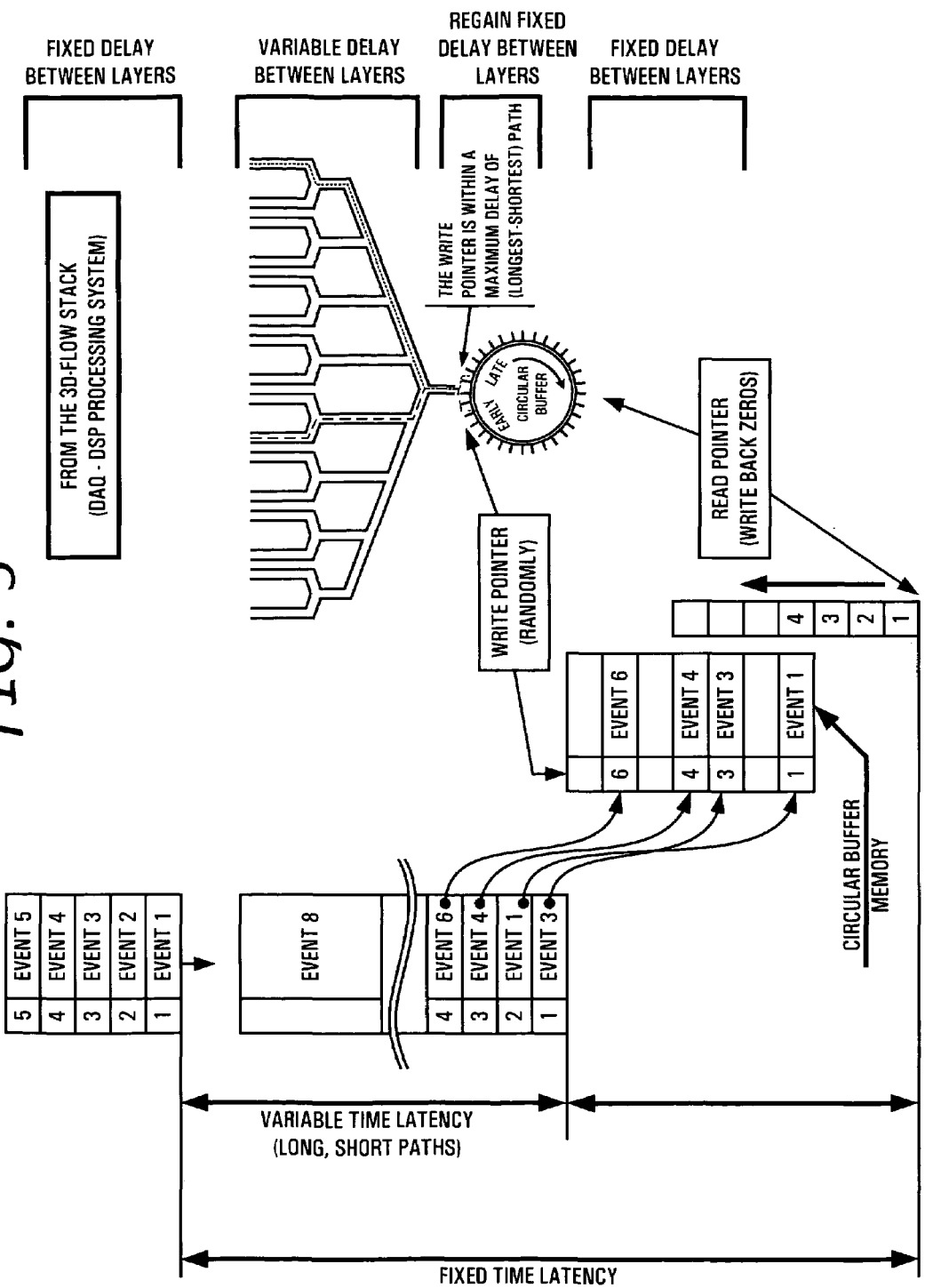
FIG. 5 depicts the flow of results (photons identified by the real-time algorithm in the 3D-Flow stack) from the data reduction stack to the coincidence circuit in accordance with an exemplary embodiment of the present invention.

FIG. 5 depicts the flow of results (photons identified by the real-time algorithm in the 3D-Flow stack) from the 3D-Flow stack to the coincidence circuit. (A stack is the section of the circuit where single photons with 511 KeV are detected.) The right side of the figure shows the flow of results from one stage of the 3D-Flow system to the next stage with the relation of the time delay of the data in different stages. The real-time algorithm and its implementation, with the 3D-Flow providing the results, is shown on the top left of FIG. 5 as output from the 3D-Flow DAQ stack and is also described in more detail in co-pending U.S. applications '904 and '532.

The circular buffer memory in the center of the figure receives the data from the last layer of the pyramid. The program loaded into the 3D-Flow processor implementing the circular buffer reads the field of the time-stamp of the event received from the pyramid and uses the value of its content to calculate the address (write-pointer) of the circular buffer where the event just received should be stored. This operation has the effect of sorting and regaining the fixed latency delay between data. At the system speed, the circular buffer is read out when all photons with a given time stamp have been stored in the circular buffer. The reading of the circular buffer(s) at any given time will provide all photons that occurred 'n' time periods before in the detector.

There are several ways of using the scheme of the circular buffer described above for detecting all possible photons belonging to a specific time period 'n.' One simple example is described herein, while an example for a more general application requiring maximum photon detection with the possibility of increasing the output bandwidth of the system is described further below. In order to find a coincidence, a signal from a detector block needs to be compared with the signal from another detector block. For the sake of convenience, the detector blocks are grouped in sectors, and only four sectors are defined in this example. All detector elements connected by lines that do not pass through the patient's body are grouped together in a sector (see top right part of FIG. 6). This scheme requires the implementation of four circuits of the type shown in FIG. 5. In accordance with an exemplary embodiment of the present invention, with one exemplary embodiment for an implementation the system comprises 1,152 separate channels. For each sampling time period, the single photon detected in each of the sectors will be compared with the photon detected in the other sectors in the 3D-Flow processors of 158 in FIG. 6. (In the very unlikely case that more than one photon is detected, the memory cell of that location is overwritten and the last value written is the one that will be compared).

Figure 6:
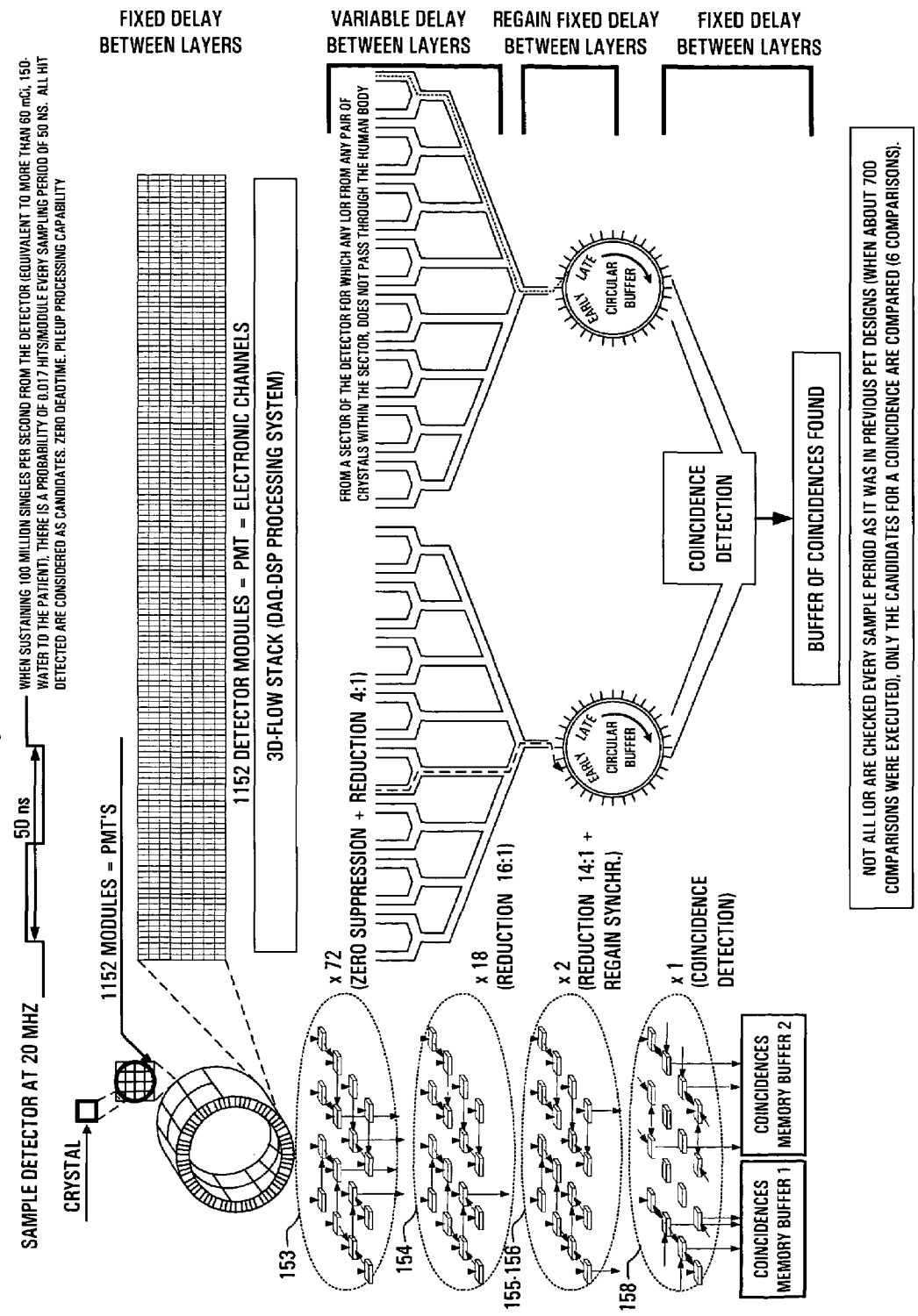
Figure 7:
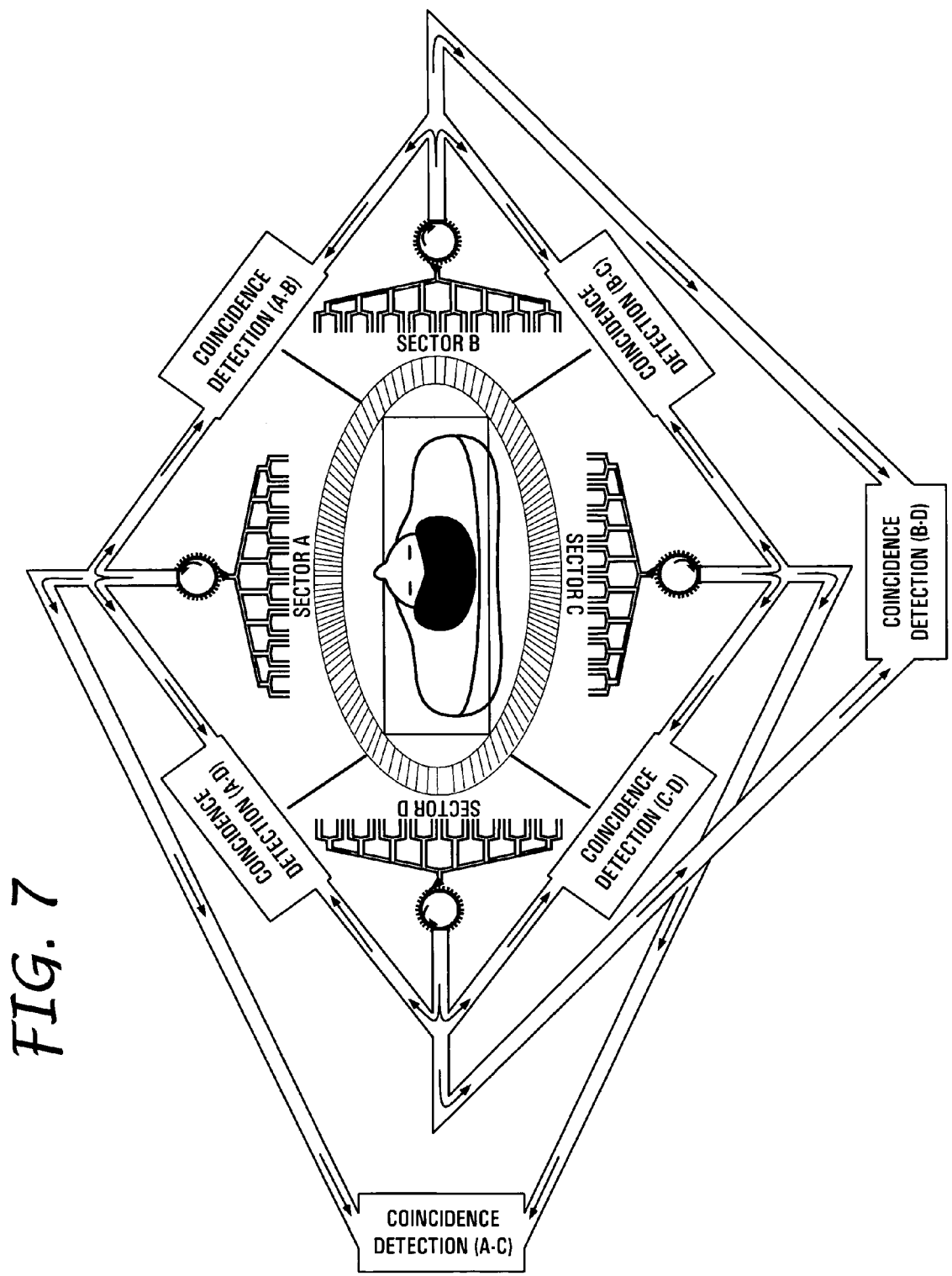
FIG. 7 depicts a coincidence detection scheme in which only those candidates found within a time of 50 ns are compared (no more than four are expected); the candidates from different detector blocks may require different numbers of clock cycles to reach the exit point, thus a sorting/resynchronizing circular buffer realigns the events in the original sequential order and within a fixed delay time from when they occurred in accordance with an exemplary embodiment of the present invention.

Only those candidates found within a time of 50 ns are compared (no more than four are expected, resulting in six comparisons being made). The candidates from different detector blocks may require different numbers of clock cycles to reach the exit point; thus, a sorting/resynchronizing circular buffer realigns the events in the original sequential order and within a fixed delay time from when they occurred. The left portion of FIG. 6 shows how many types of 3D-Flow components are required to implement the different functions. FIG. 7 shows the circuit, which requires only six comparisons amongst four photons (A-B, A-C, A-D, B-C, B-D, and C-D) every sampling period of the signals from the detector. This technique is advantageous compared to approximately 700 comparisons every 250 ns, for the prior art PET discussed above, and provides a rate of coincidences found up to 40 million coincidences per second instead of 4 million coincidences per second, as is the limitation of prior art PET devices.

The following is a general scheme, based on the requirements of the maximum radiation dose delivered to the patient and the complexity of the coincidence-detection algorithm for implementing the circuits at the output of the 3D-Flow pyramid for sorting the photons in the original sequence, regaining a fixed latency time with respect to when the event occurred in the detector, and for identifying all coincidences. The basic idea of the approach is very simple. There is no segmentation of the detector in sectors as has been done heretofore. If the radiation delivered to the patient creates $80 \times 10^6$ single photons per second, the circuit described above for sorting and realigning the latency needs to run also at $80 \times 10^6$. A single circular buffer is implemented at the speed equal to or higher than the rate of the single photon created. Each photon detected within the sampling time window of 50 ns is compared with all other photons of the same time window (e.g., six comparisons for four photons, ten for five photons, fifteen for six photons, or $(n \times (n-1))/2$), regardless of whether or not the x, y position of the two photons being compared lie along a line passing through the patient's body. A 3D-Flow processor can be used for implementing the comparison circuit. A set of 3D-Flow processors is working in parallel to perform all comparisons of detecting coincidences within a sampling period. For example, one 3D-Flow chip is sufficient for a 5 mCi dose to the patient corresponding to about $80 \times 10^6$ single photons per second activity of a PET with about 150 cm FOV. The number of comparisons are much fewer, compared to the approach used in the prior art PET devices.

The format of the sequence of bits sent out from the 3D-Flow time coincidence detection and buffer board can be the standard PET-Link format, or it can provide additional information, such as the time of flight and depth of interaction in order to allow the image reconstruction software on the workstation to build better images.

The format of the output word of the "coincidences" (pair of photons) from the 3D-Flow pyramid, time coincidence detection and buffer memory board suggested in co-pending U.S. applications '904 and '532 is the following:

bits 0–19 crystal spatial ID (hit1);
bits 20–23 Depth of inter. (hit1);
bits 24–29 photon energy (hit1);
bits 30–33 time-of-flight (hit1 and hit2);
bits 34–53 crystal spatial ID (hit2);
bits 54–57 Depth of inter. (hit2); and
bits 58–63 photon energy (hit2).

Two 20-bit fields for spatial ID of hit1 and hit2 allows for coding up to 1,048,575 crystals. Two –4-bit DOI fields allow for a depth of interaction of both hits with up to 1.56 mm resolution when crystals of 25 mm thickness are used. The energy of the two photons is coded in 64 intervals from the smallest to the highest energy value. The 4-bit field for the time of flight makes it possible to locate, within 7.5 cm resolution, the point of interaction along the line which connects the two crystals, and to measure up to 75 cm the distance in any direction inside the patient's body. The maximum measurement could be increased by changing the coincidence time window parameter. For instance, a 3-ns coincidence time window parameter will allow the measurement of any interaction that had traveled up to about 90 cm inside the patient's body. The coincidence board receives the data relative to the photons validated by the real-time algorithm executed on the 3D-Flow DAQ boards. It then performs the functionality attenuation correction described in U.S. applications '904 and '532, separating the photons found into the two modalities (PET and CT), the channel reduction and the coincidence identification. The board stores the results and the coincidences found (or the single photon validated by the algorithm for CT when the buffer memories on the DAQ boards are not installed). Results are read from two LVDS links or directly from the buffer memories by a PC CPU via the PCI bus and are sent to the graphic workstation via a standard high-speed local area network.

The technique of detecting pairs of photons in time coincidence, as described in this document and in co-pending U.S. applications '904 and '532, offers great advantages and simplifies the implementation of the hardware circuit. This technique is related to the maximum radiation dose allowed to the patient. For example, when assuming a sampling rate of the detector every 50 ns and 80 million single photons per second being the rate of "good" four photons, regardless of the number of detector electronic channels (which is assumed to be about 1800 for the proposed 140 cm FOV 3D-CBS), the number of comparisons needed will be n*(n–1)/2=(4*3)/2=6 comparisons every 50 ns, which is equivalent to 120 million comparisons per second. This task can be easily performed by current economical microprocessors (even by a FPGA electronics). By contrast, if it were necessary to achieve the same performance using the technique implemented in a prior art PET device, the number of comparisons for the same detector with about 1800 electronic channels will be n*(n–1)/4=(1800*1799)/4=809,550 comparisons every 50 ns, which is equivalent to about 16 trillion comparisons per second. This requirement has no practical solution. As a compromise, current PET manufacturers do not use full granularity of all electronic channels of the PET detector. As discussed above, one solution offered by the prior art implements a sampling rate of 250 ns based on a granularity of only 56 electronic channels, although the PET detector has 1344 electronic channels.

Cost of the 3D-CBS device is reduced, or kept at least to a minimum, through the use of low cost detector crystals. One type of scintillator crystal known for its cost effectiveness is the bismuth germanate (BGO) crystal. An even lower cost crystal is the sodium iodate (NaI) crystal; however, the disadvantages associated with NaI crystals have discouraged a large segment of the PET industry to other more expensive crystal detectors, as mentioned elsewhere above. NaI crystals are less dense and have less "stopping power" of the 511 keV photons than BGO crystals. BGO is more rugged, and allows for higher detection efficiency. Additionally, BGO is not count-rate limited, thus practitioners are encouraged to inject ever larger dosages of isotopes in their patients because the BGO can, it has been surmised, detect more counts and more counts result in clearer scans and sharper images. In fact, some estimates place BGO crystal usage at almost ten times that of NaI. Although the NaI crystal may have lower stopping power than the BGO, it provides a stronger signal.

Therefore, in accordance with another exemplary embodiment of the present invention, an improvement in the PET spatial resolution may be achieved by means of a more accurate measurement of the depth of interaction (DOI) using either low cost crystals such as BGO, or the NaI crystal which has an even lower cost. The photon's stopping power of the NaI crystal is increased by fabricating a thicker NaI detector with a stronger signal in proportion to a comparable BGO detector. With a renewed interest in NaI detectors, there is a likelihood that NaI crystals will be grown ever larger; in fact, it is technologically possible to build a single barrel to cover the entire surface of the patient's body. However, cost-efficiency criteria will most probably dictate an optimal segmentation and separation of the crystal that will cover most, but not all, of the patient's body.

Measuring the DOI is important for correcting the parallax error. Parallax is the error that results from assuming that photons strike the detector at 90 degrees to its face. With regard to FIGS. 9A–9C, a scintillation detector assembly is depicted as is well known in the prior art. The assembly comprises crystal 902, light amplifiers 904A and 904B and corresponding detectors 906A and 96B. Crystal 902 might be any type of crystal which interacts with a photon so as to produce a scintillation or rapid flash of light in the interior lattice structure of the crystal. Typically, crystal 902 is optically coupled to one or more optical amplifiers which have a detector integrated therein. Thus, as a practical matter, amplifiers 904A and 904B and corresponding detectors 906A and 906B may be Photomultipliers (PMTs), Avalanche Photodiodes (APDs) or some other type of light emitting diode; however, each amplifier-detector combination will have a signal output (a channel) for outputting the amplified signal to the processing electronics.

With regard to the parallax effect, notice from FIG. 9A that incident photon γ 900 is approaching crystal 902 at an oblique penetration (instead of being perpendicular) to the face of the crystal looking toward the emitting source. When a photon enters the crystal at 90 degrees, its X-Y position can be easily calculated from the detectors which perceive the scintillation effect in the crystal, the XY position through a centroid calculation. An exemplary centroid calculation for a 2×2 detector array (detectors A, B, C and D) is:

$$X_m = \frac{(A+B)-(C+D)}{A+B+C+D}$$

$$Y_m = \frac{(B+D)-(A+C)}{A+B+C+D}$$

(A better calculation for determining $\Delta_x$ is the ratio of the sum of the energies of all sensors at the west of the central element, divided by the sum of all sensors at the east of the central element ($\Delta_x = \Sigma E_W / \Sigma E_E$). Similarly, for the calculation of $\Delta_y$, the ratio of the sum of the energies of all sensors at the north of the central element, divided by the sum of all sensors at the south of the central element ($\Delta_y = \Sigma E_N / \Sigma E_{S'}$)).

The depth at which the photon interacts with the crystal is unimportant in this case where the photon penetrates the crystal perpendicular to the face, because it will interact somewhere along a line oriented in the Z direction formed by the intersection of an X plane and a Y plane (i.e., the LOR is found perpendicular to the X-Y planes). This presumes that all lines of response between coincidental pairs of detectors intersect the center point of the barrel which is very imprecise. In practice, once the detector elements 906 A and 906 B receive an optical signal, an analog signal is produced at output 908 and sent to the PET electronics (the coincidence board(s)). Generally, the PET electronics compare all of the possible LOR for coincidences, even those connecting two detectors, that did not receive a hit. When a coincidence is determined, the resulting LOR is used for generating the image. However, the parallax effect shifts the placement of the endpoints of the LOR along the Z axis to some default depth, such as the mid point or face of the crystal. The error is apparent on FIG. 9C, where both LOR 920 and LOR 922 are correctly spatially positioned on the X-Y plane of detector 902, but only LOR 920 is at the proper depth. Often, if a DOI calculation is not performed, the LOR is found by correspondence using a default depth (e.g., midway down the detector, on its face, etc.) The result of not calculating a DOI are graphically illustrated in FIG. 9C by the separation between LOR 920 and LOR 922.

Figure 10:
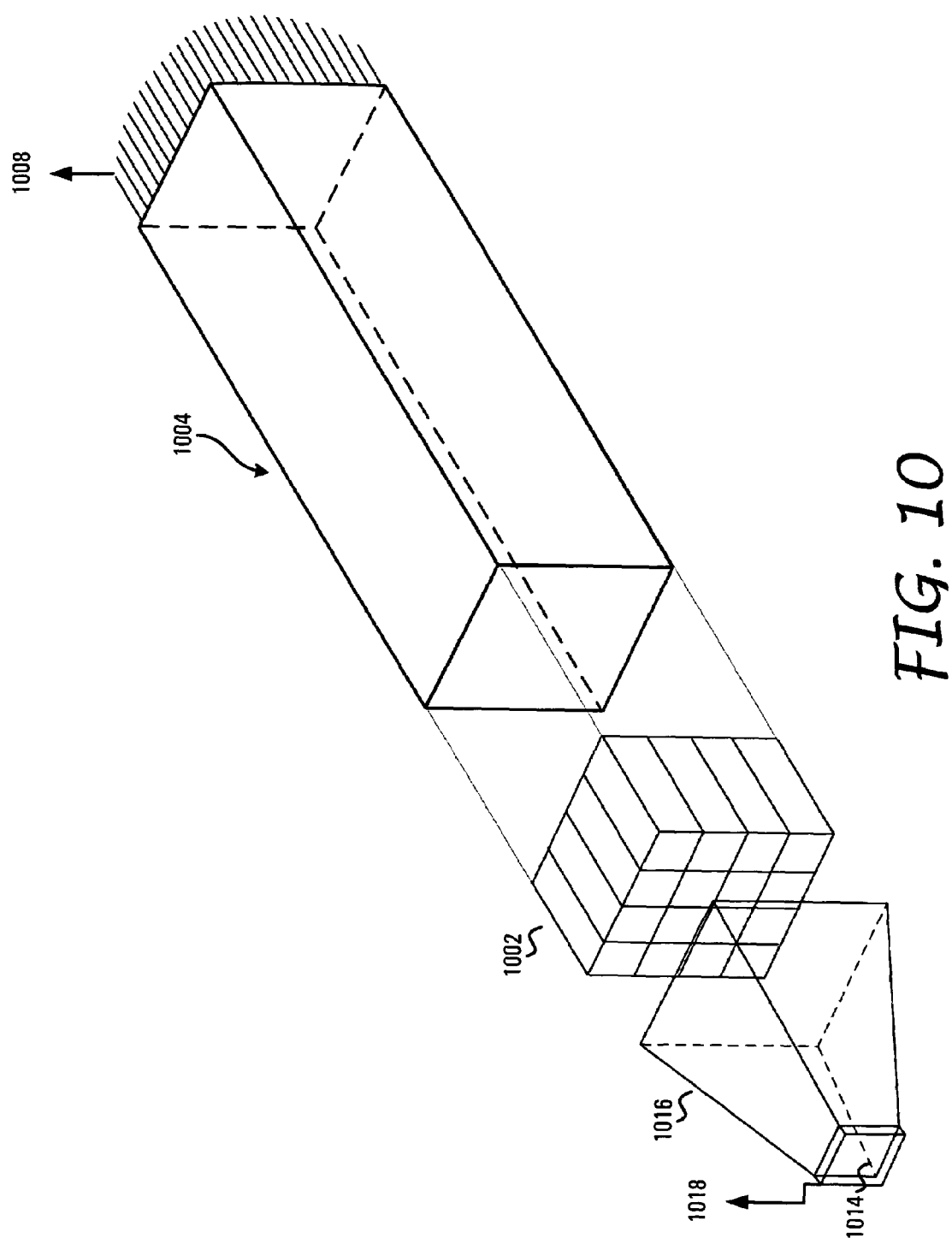
FIG. 10 is a diagram of a detector assembly having two sensors for measuring the depth of interaction to correct the parallax error in accordance with an exemplary embodiment of the present invention.

Therefore, the parallax error resulting from of incident photons with angles different from a 90-degree measurement is corrected by determining an accurate interaction depth and using the depth to properly place the LOR. DOI is determined by comparing the photon's energy, as captured by two different detectors, and relating the difference to the interaction depth of the photon in the crystal. Best results are obtained when the detectors are positioned to maximize variations in energy based on the depth of interaction. One detector should offset depth, with respect to the Z axis. In accordance with an exemplary embodiment of the present invention, the measurement of the depth of interaction to correct the parallax error of incident photons with angles different from 90 degrees can be performed by using two sensors, for instance Photomultipliers (PMT) or Avalanche Photodiodes (APD) on both sides of the detector, one internal to the barrel and the other external to the barrel. For instance, by using an array of photomultipliers internally and externally and then interpolating the signals received by the two sensors. FIG. 10 is a diagram of a detector assembly having two sensors for measuring the depth of interaction to correct the parallax error in accordance with an exemplary embodiment of the present invention. There, crystal 1002 is optically coupled to amplifier-detector 1004 and light guide 1016, which is coupled to amplifier-detector 1018. One exemplary embodiment employs Photodiodes or APD internally, rather than a PMT, to improve efficiency. Furthermore, the semiconductor will not absorb or scatter many photons that penetrate the face of the crystal because it is comprised of an extremely thin material, only a few hundred microns. In addition, because the detector obscures only a portion of the face of the crystal, not every photon penetrating the crystal's face will pass through detector 1018. Photodiodes and APD will generally cost more than PMTs and have a lower gain, those deficiencies will probably abate somewhat as the convenience of using Photodiodes or APD internally and externally becomes more apparent. In the present embodiment shown in FIG. 10, however, amplifier-sensor 1004 is depicted as a PMT, while amplifier-sensor 1014 is illustrated as an APD. The light captured by the two sensors, which is proportional to the energy of the incident photon and to the distance where the photon was absorbed by the detector with respect to the location of the two sensors, is converted into electrical signal 1008 and 1018. The two signals are converted into digital form, sent to the 3D-Flow processor which computes the interpolation of the distance from the two sensors, which is proportional to the location where the photon hit the detector. This measurement allows for more accurately determining the location where the photon hit the detector, thus eliminating the parallax error, thus improving spatial resolution. Although FIG. 10, and others, depict the detector as having been segmented into small rectangular shapes, that depiction is not intended to limit the scope of the present invention. Despite the fact that the crystal detectors may be cut in small pieces, as stated above, the entire barrel can be fabricated from several sectors, (two, four or eight arc segments). Still further, the barrel may be constructed as a single piece surrounding the entire body of the patient.

FIG. 10 shows the example of a detector assembly with a thin sensor (e.g. APD) in front of the detector (side where the radioactive source is located and the photo is hitting the detector) and a second sensor (APD or photomultiplier) on the opposite side of the detector. The light captured by the two sensors interior sensor 1014 and exterior sensor 1004, which is proportional to the energy of the incident photon and to the distance where the photon was absorbed by the detector with respect to the location of the two sensors, is converted into electrical signals 1018 and 1008, respectively. Signals 1018 and 1008 are converted into digital form, sent to the 3D-Flow processor, which computes the interpolation of the distance from the two sensors, which is proportional to the location where the photon hit the detector. This measurement determines more accurately the location where the photon hit the detector, thus eliminating the parallax error, and improving spatial resolution. Hence, PD (APD) sensor signal 1018 and PMT signal 1008 are linearly dependent on the depth of interaction (Z) from the photodetector.

Here, it should be noted that, in contrast with prior art detectors configured for DOI calculations, the 3D-CBS uses the outputs from the exterior PMTs for the vast majority of the data to be used for image generation. As mentioned above, the present system is hundreds, if not thousands, of times more efficient than prior art PET devices that use only photomultipliers. Therefore, while the 3D-CBS architecture could easily accommodate a complex interior sensor arrangement, such as an array of interior sensors, there is simply no need to expend the resources on developing interior sensors and signal channels that will be used for only one purpose—to be compared to the exterior signals for an interaction depth. To that end, the present interior sensors are chosen and configured with cost effectiveness as a primary intent. The result of the choices on the detector configuration are strikingly different than any interior sensor arrangement hereto. For instance, one means to achieve cost effectiveness is to reduce the coverage area of the APD. Notice from FIG. 10 that, although the detector (crystal) 1002 has approximately the same area as the face of exterior sensor 1004, the coverage area of the interior sensor 1014 is much smaller than the face of crystal 1004. For the purposes of the present invention, this makes absolute perfect logic. The faces of detector 1002 and exterior sensor 1004 should be comparable for better optical coupling and lowering the risk of missing an event. The requirements for coupling interior sensor 1014 are much less stringent. In fact, since what is sought from interior sensor 1014 is a reasonably accurate signal, the diode utilizes optical guide 1016 to collect and channel the scintillation from detector (crystal) 1002. In stark contrast with prior art DOI schemes, it is simply not necessary to use interior sensor 1014 for anything other than collecting an optical signal to be compared with the exterior channel signals.

Figure 11C:
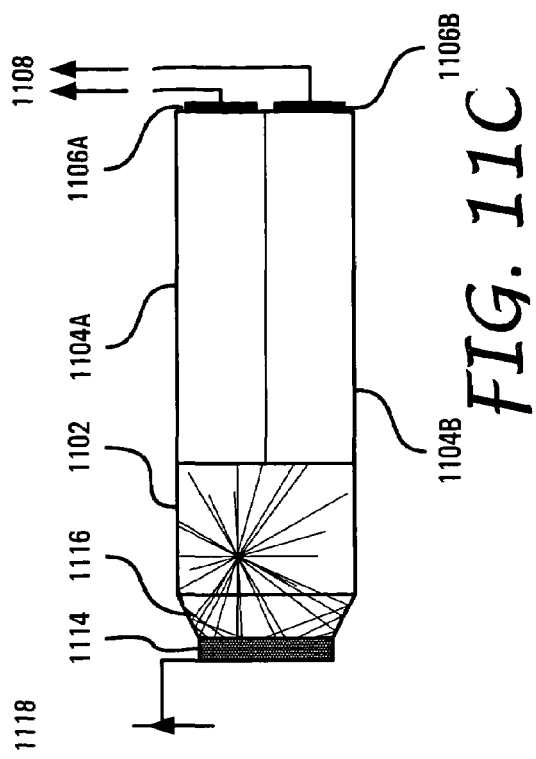
FIGS. 11A–11B depicts a scintillation detector assembly having a sensor on either end of the detector which absorbs a photon in accordance with an exemplary embodiment of the present invention.
Figure 11A:
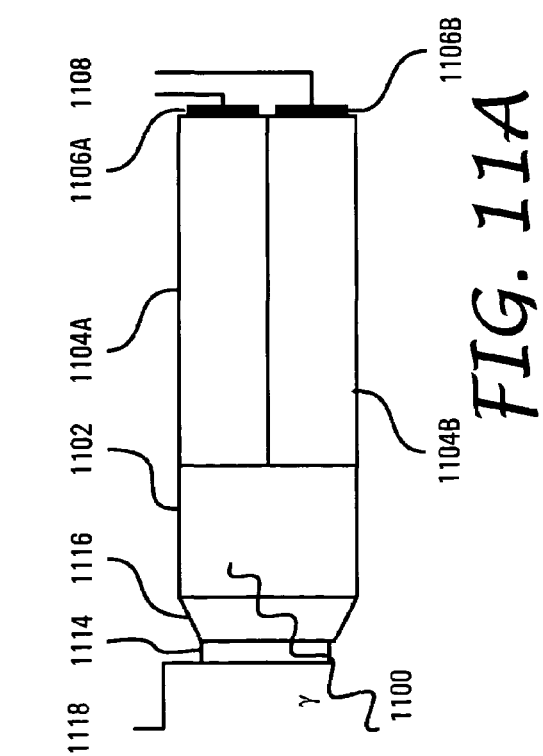
Figure 11B:
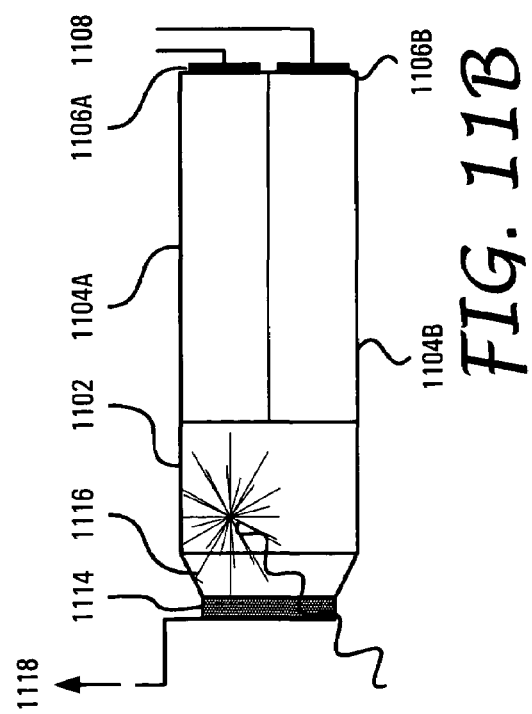

Turning now to FIGS. 11A–11B, a scintillation detector assembly having a sensor on either end of the detector is depicted absorbing a photon in accordance with an exemplary embodiment of the present invention. The assembly comprises crystal 1102, light amplifiers 1104A and 704B and corresponding detectors 1106A and 1106B. Here again, crystal 1102 may be any known or heretofore unknown type of detector which interacts with a photon to produce a scintillation or a rapid flash of light in the interior lattice structure of the crystal. Crystal 1102 is coupled to one or more optical amplifier/sensors which have a detector integrated therein. Also, as discussed with regard to FIG. 10, amplifier-sensor 1104 is depicted as an PMT, while amplifier-sensor 1114 is illustrated as an APD. Notice from FIG. 11B, however, that amplifier-sensor 1114 was the first to receive an optical signal from crystal 1102, resulting in output electrical signal 1118, while at a later time amplifier-sensor 1104 received the optical signal from crystal 1102, resulting in output electrical signal 1108. It should be cautioned, however, that the order in which the optical signals are received and the timing are relatively unimportant. The present invention utilizes the energy levels at the respective sensors, not the signal arrival times, to determine the DOI of the photon in crystal detector 1102. The depth of interaction, not the arrival times, is proportional to the respective signal strengths. In any case, once electrical signals 1108 and 1118 have been generated, they are passed to the 3D-CBS DOI electronics for integration and depth determination. To that end, optical guide 1116 collects and redirects the optical signal toward the active portion of APD 1114 in an extremely cost effective manner.

At present, the exterior sensors are PMTs for the reasons discussed above. However, correction of parallax errors from incident photons with angles different from 90 degrees can be performed by using two sensors (Photomultipliers or Avalanche Photodiodes APD) on both sides of the detector, one internal to the barrel and the other external to the barrel, for instance, by using an array of photomultipliers internally and externally and then interpolating the signals received by the two sensors. In accordance with one aspect of the present invention, Photodiodes or APD are used internally that will not absorb or scatter many photons and will significantly improve efficiency of the system because of its small thickness of material of a few hundred of microns, and a PMT is used externally. Photodiodes or APD will cost more than PMTs and have a lower gain; however, future technology advances will show that it will be convenient to use Photodiodes or APDs internally and externally. Although the present invention is using an exemplary embodiment having a detector cut (or slit) in a small rectangular shape, the present invention is not so limited to crystal detectors cut in small pieces. Instead, the present invention may be implemented having a detector with the entire barrel made of several sectors, four sectors, two sectors or, at the limit, a barrel in a single piece surrounding the entire body of the patient. This detector can have sensors (PMT, APD, or photodiodes) internally or externally to the barrel.

FIGS. 2A–2D are diagrammatic comparisons of the relationship between the increasing FOV and Lines of Response (LORs) in accordance with exemplary embodiments of the present invention. A PET with an axial FOV that is twice as long as the short FOV of the prior art PET can detect four times the number of photons in time coincidence from an organ emitting photon from the center of the FOV. FIG. 2A and FIG. 2B assume the detector has only three rings of detector elements. Only the LOR connecting opposite sets of detectors within the three rings are considered instead of all possible LORs passing through the patient's body. The top detector elements, A, B and C, and the bottom detector elements are depicted in the figure as elements D, E, F. For a linear source at the center of the FOV emitting pairs of photons in time coincidence in opposite directions, one could capture only three possible combinations AD, BE and CF (See FIG. 2A) when SEPTA are used (septa are lead rings between the ring-detectors that prevent photons arriving with an angle from hitting the detector). Thus, FIG. 2A depicts a prior art PET device with short FOV and further LOR limiting septa.

For the purpose of understanding how the capturing of photons is greater than double when the FOV is doubled, assume that the representation of the detector is simplified as shown in FIG. 2B which depicts a prior art PET with the same short FOV as in FIG. 2A, but the number of photons captured increases from three to nine when the SEPTA are removed. In the absence of SEPTA lead rings, there are nine possible combinations of pairs of photons (AD, AE, AF, BD, BE, BF, CD, CE, CF) which can be captured.

FIG. 2C depicts the effect of doubling the axial FOV has on LOR. Doubling the FOV, thereby doubling the number of detector element rings, increases the Lines of Response four times over a prior art PET device with half the number of rings (or 12 times if compared to 2-D mode, shown in FIG. 2A). If the FOV is doubled with new top detector elements G, H, L, and the new bottom detector elements M, N, P, then 36 combinations of pairs of photons emitted in opposite directions from a linear source in the center of the FOV are captured. The possible pairs for which a LOR could be drawn are: AD, AE, AF, BD, BE, BF, CD, CE, CF, plus the new GM, GN, GP, HM, HN, HP, LM, LN, LP, plus the combination of old top and new bottom AM, AN, AP, BM, BN, BP, CM, CN, CP, plus the combination of the new top and the old bottom GD, GE, GF, HD, HE, HF, LD, LE, LF.

Finally, the LOR algorithm described above is extendable; for instance, if the FOV is increased three times from that depicted in FIG. 2B, the number of pairs of photons that can be captured increases nine times (or 27 times if compared to the current use of the PET in 2-D shown in FIG. 2A). If the FOV is increased four times from that depicted in FIG. 2B, the number of pairs of photons that can be captured increases sixteen times (or 48 times if compared to the current use of the PET in 2-D shown in FIG. 2A).

Considering that most of the PETs (even the most advanced) currently available in hospitals use a 2-D mode for the torso, where only the combinations AD, BF, and CF are detected, the difference between the prior art PET and the 3D-CBS when the FOV is doubled, is from 3 to 36 (or 12 times). If the FOV of the prior art PET is tripled from 16 cm to 48 cm, then the difference in captured pairs of photons will increase 27 times when using the 3D-CBS approach.

With reference again to FIG. 1, increasing the solid angle also increases the photon capture efficiency by reducing the amount of photons lost at either end of the detector barrel. Some photons from within the detector area are also lost. Some quantity of photons that emanate from the part of the body that is covered by the detector leave the body at an angle that allows them to escape the detector through the openings between the detector segments. This quantity can be calculated as a percentage of the perimeter of a circle drawn around the lengthwise cross section of the entire detector not covered by the 16 cm FOV barrel.

Increasing the FOV inherently results in increasing the solid angle and thus capturing more photons, but in addition to FOV, decreasing the diameters of the barrel opening also limits the solid angle. Typically, the barrel of a prior art PET device is implemented with a constant diameter throughout and since prior art PET devices are typically configured having the barrel's diameter sufficiently large enough to accommodate the most robust patient body shapes, the solid angle is high and photons are lost at the barrel's ends. The solid angle of the present invention, on the other hand, is limited by the FOV, but also by the diameters of the rings of the barrel being separately adjustable for the corresponding portion of the patient. Thus, in accordance with an exemplary embodiment of the present invention, the rings at the patient's head and legs may be separately configured with a much smaller diameter than those rings corresponding to the patient's torso, thereby greatly limiting the solid angle and reducing the amount of photons lost at the barrel's open ends (see U.S. patent application Ser. No. 10/453,255 (hereinafter U.S. application '255) entitled "Gantry for Geometrically Configurable and Non-configurable Positron Emission Tomography Detector Arrays."

With further regard to the barrel, the entire structure may be treated as one or two cameras which process photon events received within one group of 32×64 Photomultipliers (PMTs) or two groups 32×32 PMTs, rather than hundreds of groups of 2×2 PMTs. It should be understood that, rather than a PMT, an Avalanche Photodiodes (APDs) or some other type of light emitting diode may be substituted; however, each amplifier-detector combination will have a signal output (a channel) for outputting the amplified signal to the processing electronics. This is accomplished, in accordance with other exemplary embodiments of the present invention, by eliminating the boundaries between crystals and between small groups of PMTs (see U.S. applications '207, '904 and '532 and especially '024 and '255). Typically, prior art PET devices utilize a block detector design concept in which a single crystal is optically coupled to a 2×2 block (or module) of PMTs.

FIG. 3A is a diagram of a prior art detector crystal optically coupled to a 2×2 PMT module. A boundary is established between each 2×2 PMT module 304 and similarly between each crystal 302. Each 2×2 PMT module 304 is treated by the PET as a small camera and photon impacts are independently processed. For example, when photon 300 impacts crystal 302 and is received at 2×2 PMT module 304, the event is processed independently of every other 2×2 PMT module. If 2×2 PMT module 304 cannot identify a signal as being a photon impact, the boundary does not allow the recipient module to compare its signal with its neighbors and that photon is lost. The identification of the crystal of interaction in the 2×2 PMT block is made using only the four PMTs in the module.

Because communication between adjacent 2×2 PMT modules is impossible, centroid calculations are necessarily dependent on the separate 2×2 PMT modules and lack information from adjacent modules that is necessary for accurately determining the point of impact for the photon.

Crystal 302 (coupled to prior art PMT module 304) is typically subdivided into an 8×8 block of variable length slits. The 8×8 block does not share light well with adjacent 8×8 crystal blocks. Moreover, edge and corner subdivisions of each prior art 8×8 crystal block contribute only a small signal compared to the contribution of the inner subdivisions of the crystal making the identification of photon events more difficult, and lowering the overall efficiency for the PET. Furthermore, if a photon strikes the boundary edge between adjacent 2×2 PMT modules (between the edge and/or corner subdivisions of two 8×8 crystal blocks), neither PMT may receive sufficient energy to recognize the strike as a photon and the photon is lost, further reducing the efficiency of capturing photons for the prior art PET device.

Figure 3B:
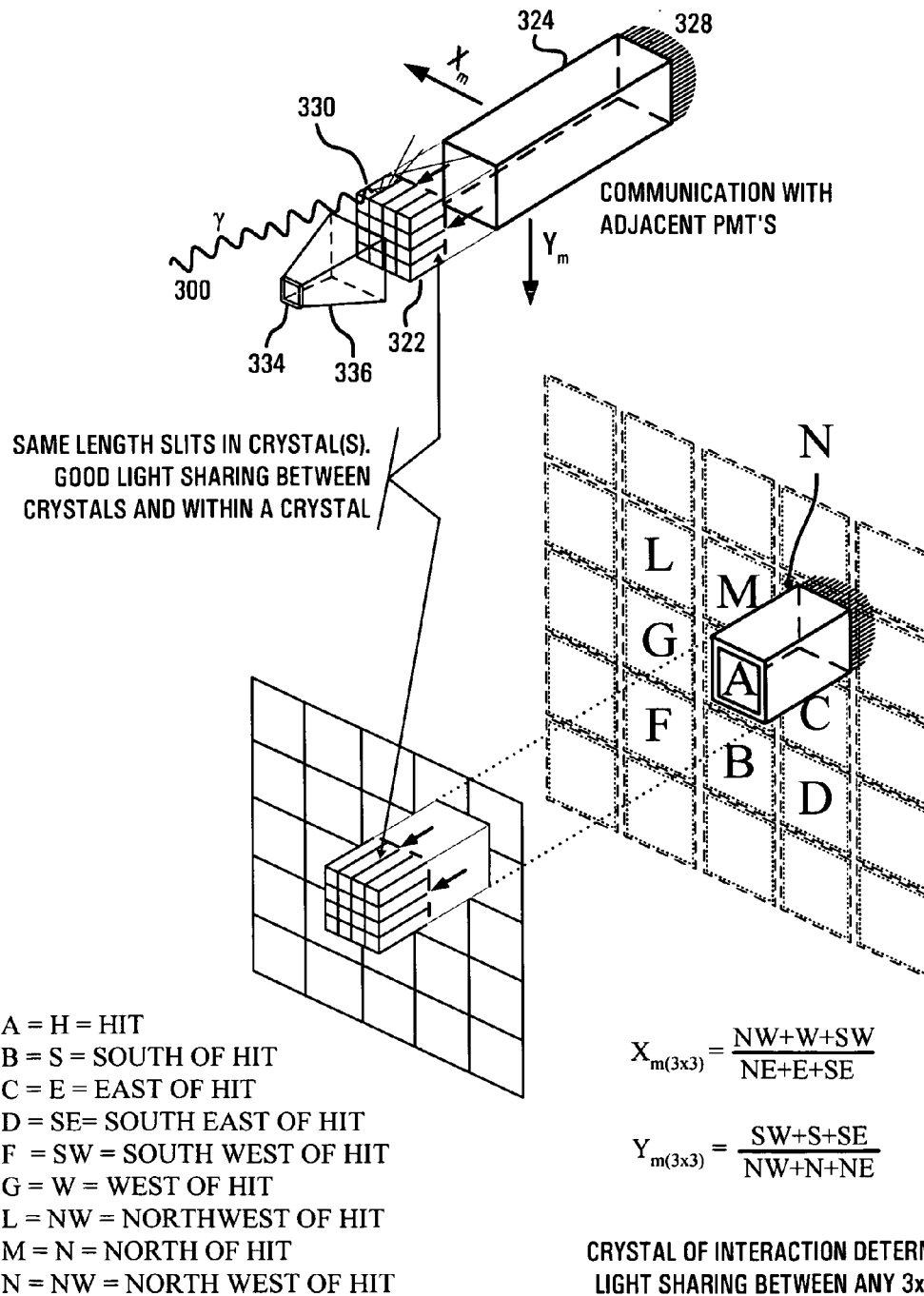
FIG. 3B is a diagram of a detector crystal optically coupled to a PMT in accordance with an exemplary embodiment of the present invention.

In accordance with exemplary embodiments of the present invention, these problems are overcome by permitting each PMT to share and receive information (signals) with its neighbor PMT, and further by permitting the crystal to have the same degree of light sharing throughout (or with adjacent crystals) by using slits of equal length (or no slits), thereby allowing sharing of the light with adjacent PMTs in all four directions with no boundaries. FIG. 3B is a diagram of detector crystal optically coupled to a PMT in accordance with an exemplary embodiment of the present invention. By treating the PET as one large camera, rather than hundreds of smaller cameras, photon impacts are more readily identified than the prior art because there is no boundary limitation on where a PMT may get information. Signals for photon impacts occurring on the edges and corner blocks associated with PMT 324 are shared with its neighbors without regard to any boundary; consequently, photon impacts on the edges, corners and between PMTs are much more readily identified as a photon incidence.

The point of impact of a photon may be accurately calculated using essentially a two-step process without regard to boundaries in accordance with another exemplary embodiment of the present invention. The process comprises finding a local maxima for an impact and then calculating the precise point of impact of the photon in a PMT cluster of a predetermined size (2×2, 3×3, 4×4, 5×5 and so on). The local maxima is defined as the head of a cluster of PMTs (of a predetermined size 2×2, 3×3, etc.) which corresponds to the location of the incident photon. The local maxima is found by checking the signal (and arrival time) at a PMT with similar information in the neighboring channels. When the local maxima is determined, the photon's energy can be calculated by summing the energy of the local maxima with its neighbor's energies (e.g., for a 3×3 PMT cluster Energy=NW+N+NE+W+C+E+SW+S+SE). The photon's precise point of impact may then be determined by sharing light between ANY predefined cluster of PMTs (e.g., a 3×3 PMT cluster).

Finally, and as alluded to above, perhaps the single most cost effective area of focus for increasing PET efficiency is in the processing electronics. Within the electrons, two primary areas exist which limit the efficiency of the prior art PET. The first involves limitations of prior art electronics to identify valid photons, and the second involves limitations of prior art electronics for identifying photons in time coincidence.

It is recognized that prior art PETs capture only 0.2 million pairs per second of the original, 1,424 million pairs of photons per second emitted by tracer within the patient's body. It has been further proposed that approximately 2.6 million pairs of photons per second are remaining after the natural phenomenon of photons being scattered or absorbed in the patient, the smaller FOV and smaller solid of prior art PET devices, and the inherent inefficiency of a crystal photon detector. Thus, of the 2.6 million pairs of photons per second remaining, 2.4 million pairs of photons are lost per second due to deficiencies in the electronics and the detector design which accounts for the prior art PETs capturing only 0.2 million pairs per second. Therefore, vast increases in photon capture efficiency may be achieved by increasing the efficiency in the prior art PET device electronics.

It should also be noted that a paradox exists when attempting to increase the efficiency of the prior art PET device by implementing the above-described improvements in the present PET with respect to FOV, solid angle and boundary elimination. That paradox exists because the processing electronics of prior art PET devices cannot efficiently process the level of data generated by the prior art PET device, and therefore the prior art electronics could never accommodate the increased amount of data resulting from implementing the modifications described above. Therefore, the inefficiencies in the prior art electrons must be rectified before any appreciable increase in efficiencies is realized from other modifications.

One shortcoming in the prior art electronics is a consequence of a bottleneck in the incoming data which occurs because the prior art detector is typically segmented into approximately 56 modules (depending on the PET's manufacturer). Since each module covers a large detector area, when crystals with slow decay time are used, the entire module is unable to acquire data (dead time) for 1 to 2 μs when a photon hit is detected. Thus, photons may be received continuously from the same module only at a maximum rate of 0.5 to 1 MHz (for an activity of about 100×106 single photons per second received from a detector with 56 modules, there is a 44% probability that a photon will hit a module during a sampling time period of 250 ns).

In accordance with an exemplary embodiment of the present invention, a data acquisition and processing electronics board has been developed for high efficiency photon detection in PET/CT applications. The board comprises sixty-eight processors (3D-Flow™ processors), each capable of executing up to 26 operations in a single cycle. These processors can execute a programmable real-time algorithm that acquires and processes input data with zero dead-time, thus improving the signal-to-noise ratio, and at best, extracts the characteristic parameters of the interaction between the incident photon and different types of detectors (slow: NaI(TI), BGO, etc. or fast: LSO, GSO, etc.). It can trigger on any electronic channel and can accurately measure incident photon energy by summing 9, 16, or 25 elements. Spatial resolution can be accurately measured on ANY cluster of 3×3 (or 5×5, either of which are predefined) PMTs. Additionally, each processor can execute complex real-time algorithms to accurately measure DOI and eliminate the parallax error of oblique photons. Timing is controlled by two in-phase clocks at 20 MHz and 40 MHz (with PLL×8=320 MHz internal clock) with a skew <40 ps between any processor clock in the system. A Time-to-Digital converter (TDC) measures arrival time and assigns a time stamp to the photon at each channel with 500 ps resolution. The board has 2,211 components with >20,000 pins connected with about 9,000 nets in a PCB with only eight layers of signals and six layers for power and ground. The board is suitable for use with prior art PETs having different detector types and for the 3D-CBS for best PET efficiency improvement.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A device for detecting subatomic particles comprising:
   a detector assembly, said detector assembly comprising:
   a first plurality of transducers; and
   at least one detector crystal optically coupled to at least some of said first plurality of transducers, wherein a single detector crystal in said at least one detector crystal has a plurality of slits, each slit being approximately equivalent in length as each other slit and said plurality of slits being oriented parallel to the optical axis of said at least some of said first plurality of transducers;
   a plurality of processors, said plurality of processors being arranged in a plurality of substantially parallel layers, and some processors in said plurality of processors being capable of communicating with processors to each lateral side in one substantially parallel layer, receiving communication from a processor in a second substantially parallel layer and transmitting to a third processor in a third substantially parallel layer; and wherein
   each transducer in the first plurality of transducers is in electrical communication with at least one processor in the plurality of processors.

2. The device recited in claim 1 above, wherein said at least one detector crystal forms a first side and an opposing second side and wherein said first plurality of transducers are optically coupled to said first side, the detector assembly further: comprising:
   a second plurality of transducers, said second plurality of transducers optically coupled to the at least one detector crystal, the second plurality of transducers being coaxial with at least some of the first plurality of transducers, wherein said second plurality of transducers are optically coupled to said second side, and wherein a surface area of a face of a transducer in said second plurality of transducers is smaller than a surface area of a face of a transducer in said first plurality of transducers; and wherein each transducer in the second plurality of transducers is in electrical communication with at least one processor in said plurality of processors.

3. The device recited in claim 2 above, wherein a light guide is optically coupled between a detector crystal in the at least one detector crystal and a transducer in the second plurality of transducers.

4. The device recited in claim 2 above, wherein at least one of the plurality of processors performs a depth of interaction calculation.

5. The device recited in claim 2 above, wherein a transducer in said second plurality of transducers is a photomultiplier (PMT), an avalanche photodiode (APD), or a photodiode.

6. The device recited in claim 2 above, wherein said at least one detector crystal defines a barrel around a patient and wherein the first plurality of transducers are arranged on an exterior face of said barrel and said second plurality of transducers are arranged on an interior face of said barrel.

7. The device recited in claim 6 above, wherein said at least one detector crystal is a single detector crystal.

8. The device recited in claim 6 above, wherein said barrel is segmented into sectors, and wherein said at least one detector crystal consists of four separate detector crystals, each detector crystal in said four separate detector crystals occupying a different sector of said barrel.

9. The device recited in claim 6 above, wherein said barrel is segmented into sectors, and wherein said at least one detector crystal consists of two separate detector crystals, each detector crystal in said two separate detector crystals occupying a different sector of said barrel.

10. The device recited in claim 2 above, wherein
   a first transducer in the first plurality of transducers is in electrical communication with a first processor in said plurality of processors; and
   a second transducer in said second plurality of transducers is in electrical communication with said first processor.

11. The device recited in claim 10 above, wherein said first processor is in a first substantially parallel layer in said plurality of substantially parallel layers and wherein said first processor is in electrical communication with four other processors in said first substantially parallel layer.

12. The device recited in claim 11, wherein said first processor is in electrical communication with a second processor in a second substantially parallel layer in said plurality of substantially parallel layers.

13. The device recited in claim 1 above, the device further comprising a pyramidal funneling structure, said pyramidal funneling structure comprising a plurality of funnel input processors, and wherein a funnel input processor in the plurality of funnel input processors is coupled to a processor in the plurality of processors of claim 1.

14. The device recited in claim 1 above, wherein a transducer in said first plurality of transducers is a photomultiplier (PMT) or an avalanche photodiode (APD).

15. The device recited in claim 1 above, wherein a detector crystal in the at least one detector crystal is a bismuth germinate (BGO) crystal or a sodium iodate (NaI) crystal.

16. The device recited in claim 1 above, wherein a processor in said plurality of processors is a FPGA.

17. The device recited in claim 1 above, wherein a processor in said plurality of processors is an ASIC.

18. The device recited in claim 1 above, wherein the timing of a processor in said plurality of processors is provided by two in-phase clocks at 20 MHz and 40 MHz.

19. The device recited in claim 1, wherein the subatomic particles are photon pairs.

* * * * *